US009260714B2

(12) United States Patent
Chen et al.

(10) Patent No.: US 9,260,714 B2
(45) Date of Patent: Feb. 16, 2016

(54) SUPPRESSION OF NON-SPECIFIC AMPLIFICATION WITH HIGH-HOMOLOGY OLIGONUCLEOTIDES

(71) Applicant: Roche Molecular Systems, Inc., Pleasanton, CA (US)

(72) Inventors: Xiaoying Chen, Alameda, CA (US); Suzanne Cheng, Oakland, CA (US); Thomas W. Myers, Sunnyvale, CA (US); Nancy Patten, Oakland, CA (US); Nancy Schoenbrunner, Moraga, CA (US); Sim C. Truong, Union City, CA (US)

(73) Assignee: ROCHE MOLECULAR SYSTEMS, INC., Plesanton, CA (US)

( * ) Notice: Subject to any disclaimer, the term of this patent is extended or adjusted under 35 U.S.C. 154(b) by 0 days.

(21) Appl. No.: 13/682,547

(22) Filed: Nov. 20, 2012

(65) Prior Publication Data
US 2013/0177946 A1    Jul. 11, 2013

Related U.S. Application Data

(60) Provisional application No. 61/566,518, filed on Dec. 2, 2011.

(51) Int. Cl.
*C12Q 1/68* (2006.01)
*C12N 15/11* (2006.01)
*G06F 19/12* (2011.01)
*G06F 19/22* (2011.01)

(52) U.S. Cl.
CPC .............. *C12N 15/11* (2013.01); *C12Q 1/6848* (2013.01); *C12Q 1/6858* (2013.01); *G06F 19/12* (2013.01); *G06F 19/22* (2013.01)

(58) Field of Classification Search
None
See application file for complete search history.

(56) References Cited

U.S. PATENT DOCUMENTS

| | | | |
|---|---|---|---|
| 2007/0117118 A1 | 5/2007 | Yaku et al. | |
| 2007/0224208 A1 * | 9/2007 | Guo et al. ................ | 424/184.1 |
| 2009/0023190 A1 | 1/2009 | Lao et al. | |
| 2009/0053720 A1 * | 2/2009 | Newton ............................ | 435/6 |
| 2010/0285478 A1 * | 11/2010 | Chen et al. ...................... | 435/6 |
| 2011/0229939 A1 | 9/2011 | Yaku et al. | |

FOREIGN PATENT DOCUMENTS

| | | |
|---|---|---|
| WO | WO02057487 A2 | 7/2002 |
| WO | WO 2005047542 A1 * | 5/2005 |
| WO | WO2011104758 A1 | 9/2011 |
| WO | PCT/EP2012/004944 | 3/2013 |

OTHER PUBLICATIONS

Snove et al. (Many commonly used siRNAs risk off-target activity, Biochemical and Biophysical Research Communications 319 (2004) 256-263).*
Parsons et al. (Allele-Specific Competitive Blocker-PCR Detection of Rare Base Substitution, In: Methods in Molecular Biology, vol. 291, Molecular Toxicology Protocols, 2005).*
Gorden et al. (Analysis of BRAF and N-RAS Mutations in Metastatic Melanoma Tissues, Cancer Research 63, 3955-3957, Jul. 15, 2003).*
Yao et al. (PrimerSNP: a web tool for whole-genome selection of allele-specific and common primers of phylogenetically-related bacterial genomic sequences, BMC Microbiology 2008, 8:185).*
Chen BLAST (attached; Sep. 26, 2013)).*
Parsons BLAST, attached Sep. 26, 2013).*
Snove BLAST, attached, Sep. 26, 2013).*
McKinzie & Parsons (Detection of rare K-ras codon 12 mutations using allele-specific competitive blocker PCR, Mutation Research 517 (2002) 209-220).*
Evans & Segal (Novel multiplex allele-specific PCR assays for the detection of resistance to second-line drugs in *Mycobacterium tuberculosis*, J Antimicrob Chemother 2010; 65: 897-900).*
Vallone et al. (A multiplex allele-specific primer extension assay for forensically informative SNPs distributed throughout the mitochondrial genome, Int J Legal Med (2004) 118 : 147-157).*
Chou et al. (A single-tube, sensitive multiplex method for screening of isocitrate dehydrogenase 1 (IDH1) mutations, Blood, Jul. 22, 2010 vol. 116, No. 3).*
Bezieau et al. (High Incidence of N and K-Ras Activating Mutations in Multiple Myeloma and Primary Plasma Cell Leukemia at Diagnosis, Human Mutation 18:212-224 (2001)).*
Alexander et al. (Drop-In, Drop-Out Allele-Specific PCR, Mol. Biotech., vol. 28, 2004).*
Chen homology, attached, accessed Feb. 21, 2014.*
Weiner et al. (Kits and their unique role in molecular biology: a brief retrospective, BioTechniques 44:701-704 (25th Anniversary Issue, Apr. 2008)).*
Stratagene ("Gene Characterization Kits" 1988).*
Munzel et al. (5-Hydroxymethylcytosine, the Sixth Base of the Genome, Angew. Chem. Int. Ed. 2011, 50, 6460-6468).*
Ballantyne et al. (Locked nucleic acids in PCR primers increase sensitivity and performance, Genomics 91 (2008) 301-305).*
Meltzer BLAST (attached, NCBI BLAST Website, Apr. 10, 2015).*
Meltzer BLAST align, attached, accessed Jul. 17, 2015.*
Meltzer BLAST, attached, accessed Jul. 17, 2015).*
Meltzer alignments, attached, BLAST alignment from NCBI BLAST, Aug. 31, 2015.*
Hua, Yimin, et al., 2008, "Antisense Masking of an hnRNP A1/A2 !Itronic Splicing Silencer Corrects SMN2 Splicing in Transgenic Mice", The American Journal of Human Genetics, 82:834-848.
Philipp, Katrin, et al., 2005, "TGF-B antisense oligonucleotides reduce mRNA expression of matrix metalloproteinases in cultured wound-healing-related cells", International Journal of Molecular Medicine, 15:299-303.
Kim N.W., Advances in quantification and characterization of, Nucleic Acids Research, 1997, pp. 2595-2597, vol. 25, No. 13.

\* cited by examiner

*Primary Examiner* — Christopher M Babic
*Assistant Examiner* — Aaron Priest
(74) *Attorney, Agent, or Firm* — Carol Johns; Olga Kay

(57) ABSTRACT

The invention comprises suppressor oligonucleotides for reducing amplification of a non-target nucleic acid sequences; the method of designing and using such oligonucleotides, as well as kits and reaction mixtures.

7 Claims, 20 Drawing Sheets

FIGURE 8

| SEQ ID | Length | Total Hits | Hits w/Criteria | Degree of Homology | Breakthrough |
|---|---|---|---|---|---|
| SEQ ID NO: 1 | 19 | 3973 | >20 | High | No |
| SEQ ID NO: 2 | 20 | 1118 | 6 | Medium | No |
| SEQ ID NO: 3 | 21 | 1939 | 3 | Medium | No |
| SEQ ID NO: 4 | 20 | 426 | 6 | Medium | No |
| SEQ ID NO: 5 | 24 | 1954 | 3 | Medium | No |
| SEQ ID NO: 24 | 26 | 911 | 1 | Low | Yes |
| SEQ ID NO: 25 | 26 | 328 | 1 | Low | Yes |
| SEQ ID NO: 26 | 28 | 926 | 1 | Low | Yes |

SEQUENCE LISTING

<160> NUMBER OF SEQ ID NOS: 99

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctaccactgg gcctcacct                                                19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caggatcagg tcagcgggct                                               20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agacaggatc aggtcagcgg g                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caggtcagcg ggctaccact                                                20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acaagtgaga gacaggatca ggtc                                           24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctggtggtgg ttggagccgc                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: N4-Methyl-dC

<400> SEQUENCE: 7
ctgctggtgg ttggagcagc                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:

<221> NAME/KEY: modified_base
<222> LOCATION: (18)..(18)
<223> OTHER INFORMATION: N6-Methyl-dA

<400> SEQUENCE: 8
ctgctggtgg ttggagcagc                                          20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caaactggtg gtggttggag ctt                                      23

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacaaactgg tggtggttgg agctt                                    25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: N6-tertiary-butyl-benzyl-dA

<400> SEQUENCE: 11
cagagtggtg gtggttggag cat                                      23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(20)
<223> OTHER INFORMATION: N6-tertiary-butyl-benzyl-dA

<400> SEQUENCE: 12
aagtggtggt ggttggagca ga                                       22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)

<223> OTHER INFORMATION: N6-Methyl-dA

<400> SEQUENCE: 13
aacttggtgg tggttggagt aga                                         23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aactggtggt ggttggagct ga                                          22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aactggtggt ggttggaaca c                                           21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aactggtggt ggttggatca c                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: N4-tertiary-butyl-benzyl-dC

<400> SEQUENCE: 17
atcgggtggt ggttggagca c                                           21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: N4-tertiary-butyl-benzyl-dC

<400> SEQUENCE: 18
cagactggtg gtggttggag caa                                         23

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: N6-tertiary-butyl-benzyl-dA

<400> SEQUENCE: 19
agactggtgg tggttggagc aa                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(20)
<223> OTHER INFORMATION: N4-tertiary-butyl-benzyl-dC

<400> SEQUENCE: 20
agactggtgg tggttggagc aa                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aactggtggt ggttggagca at                                              22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aactggtggt ggttggagca tt                                              22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(19)
<223> OTHER INFORMATION: N4-Methyl-dC

<400> SEQUENCE: 23
aactggtggt ggttggagca at                                              22

<210> SEQ ID NO 24
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaatatgggt aaagatgatc cgacaa                                          26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtaaagatga tccgacaagt gagaga                                          26

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaatatgggt aaagatgatc cgacaagt                                        28

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX
<220> FEATURE:
<221> NAME/KEY: modified_base
<222> LOCATION: (7)..(7)
<223> OTHER INFORMATION: N4-Methyl-dC
<220> FEATURE:
<223> OTHER INFORMATION: 3'-Phosphate

<400> SEQUENCE: 27
cactgaccaa tccagctaat ccagaaccac                                      30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX
<220> FEATURE:
<221> NAME/KEY: modified_base
<222> LOCATION: (7)..(7)
<223> OTHER INFORMATION: N4-Methyl-dC
<220> FEATURE:
<223> OTHER INFORMATION: 3'-Phosphate

<400> SEQUENCE: 28
cactgaccaa tccagctaat ccagaaccac                                      30
```

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-HEX
<220> FEATURE:
<221> NAME/KEY: modified_base
<222> LOCATION: (7)..(7)
<223> OTHER INFORMATION: N4-Methyl-dC
<220> FEATURE:
<223> OTHER INFORMATION: 3'-Phosphate

<400> SEQUENCE: 29
gtggttcctg gattagctgg attgtcagtg                                    30

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N6-tertiary-butyl-benzyl-dA

<400> SEQUENCE: 30
ggatatactg gatacagctg gacat                                         25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggacatactg gatacagctg gactt                                         25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggacatactg gatacagctg gagat                                         25

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acatactgga tacagctgga ctc                                           23

<210> SEQ ID NO 34

<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atactggata cagctggact c                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atactggata cagctggata c                                              21

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: Inosine

<400> SEQUENCE: 36
tggatatact ggatacagct gnaa                                           24

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gacatactgg atacagctgg aa                                             22

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: N6-Methyl-dA

<400> SEQUENCE: 38
tggatatact ggatacagct ggaa                                           24

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (22)..(22)
<223> OTHER INFORMATION: N4-tertiary-butyl-benzyl-dC

<400> SEQUENCE: 39
gagatactgg atacagctgg act                                          23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gacatactgg atacagctgt act                                          23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gacatactgg atacagctga act                                          23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: N4-tertiary-butyl-benzyl-dC

<400> SEQUENCE: 42
gacgtactgg atacagctgg acc                                          23

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(20)
<223> OTHER INFORMATION: N4-tertiary-butyl-benzyl-dC

<400> SEQUENCE: 43
cgtactggat acagctggac c                                            21

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
```

```
gacatactgg atacagctga acc                                          23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: N4-Methyl-dC

<400> SEQUENCE: 45
gacatactgg atacagctgg tcg                                          23

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: N4-tertiary-butyl-benzyl-dC

<400> SEQUENCE: 46
acgtactgga tacagctgga cg                                           22

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(22)
<223> OTHER INFORMATION: N4-tertiary-butyl-benzyl-dC

<400> SEQUENCE: 47
gacacactgg atacagctgg acg                                          23

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agagaaaata atgctcctag tacctgtag                                    29

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tcctttcaga gaaaataatg ctcctagt                                     28
```

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gttaatatcc gcaaatgact tgctattatt                                    30

<210> SEQ ID NO 51
<211> LENGTH: 33
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<221> NAME/KEY: modified_base
<222> LOCATION: (7)..(7)
<223> OTHER INFORMATION: N4-Methyl-dC
<220> FEATURE:
<223> OTHER INFORMATION: 3'-Phosphate

<400> SEQUENCE: 51
ctgtccctca tgtattggtc tctcatggca ctg                                33

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<221> NAME/KEY: modified_base
<222> LOCATION: (7)..(7)
<223> OTHER INFORMATION: N4-Methyl-dC
<220> FEATURE:
<223> OTHER INFORMATION: 3'-Phosphate

<400> SEQUENCE: 52
ctcatgctat tggtctctca tggcactgta c                                  31

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<221> NAME/KEY: modified_base
<222> LOCATION: (7)..(7)
<223> OTHER INFORMATION: N4-Methyl-dC
<220> FEATURE:
<223> OTHER INFORMATION: 3'-Phosphate

<400> SEQUENCE: 53
cttcgccctg tcctcatgta ttggtctctc                                    30

<210> SEQ ID NO 54

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
catgaaacaa atgaatgatg cacatcctc                                    29

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
catgaaacaa atgaatgatg cacatcgtc                                    29

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
catgaaacaa atgaatgatg cacattatc                                    29

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caatgcatgc tgtttaattg tgtgga                                       26

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttcagttcaa tgcatgctgt ttaattgtg                                    29

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtggaatcca gagtgagctt tcat                                         24

<210> SEQ ID NO 60
<211> LENGTH: 11

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-JA270
<220> FEATURE:
<223> OTHER INFORMATION: 3'-BHQ-2

<400> SEQUENCE: 60
tggctggaca a                                                          11

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-JA270
<220> FEATURE:
<223> OTHER INFORMATION: 3'-BHQ-2

<400> SEQUENCE: 61
atggattgga                                                            10

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aaagaattgg atctggatca ttagc                                           25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aaagaattgg atctggatca ttcgc                                           25

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aaagaattgg atctggatca tgtgc                                           25

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 65
aaagaattgg atctggatca tata                                          24

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acaaagaatt ggatctggat cattaa                                        26

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agtgggacaa agaattggat cagt                                          24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agtgggacaa agaattggat ctat                                          24

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acaaagaatt ggatctggat catttaa                                       27

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gacaaagaat tggatctgga tcatttaa                                      28

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
```

```
gcgaacagtg aatatttcct ttgatg                                          26
```

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

```
gacttgtcac aatgtcacca cattacata                                       29
```

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<223> OTHER INFORMATION: 3'-BHQ-2

<400> SEQUENCE: 73

```
agtctacaag                                                            10
```

<210> SEQ ID NO 74
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<223> OTHER INFORMATION: 3'-BHQ-2

<400> SEQUENCE: 74

```
tggcatggta                                                            10
```

<210> SEQ ID NO 75
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-tertiary-butyl-benzyl-dA

<400> SEQUENCE: 75

```
agtaagaata ggtgattttg gtctagctac aa                                   32
```

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: N4-tertiary-butyl-benzyl-dC

```
<400> SEQUENCE: 76
agtaagaata ggtgattttg gtctagctac aa                                    32

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(30)
<223> OTHER INFORMATION: N4-tertiary-butyl-benzyl-dC

<400> SEQUENCE: 77
agtaagaata ggtgattttg gtctagctcc aa                                    32

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (31)..(31)
<223> OTHER INFORMATION: N6-tertiary-butyl-benzyl-dA

<400> SEQUENCE: 78
agtaagaata ggtgattttg ntctagctac at                                    32

<210> SEQ ID NO 79
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(26)
<223> OTHER INFORMATION: Inosine
<220> FEATURE:
<221> NAME/KEY: modified_base
<222> LOCATION: (31)..(31)
<223> OTHER INFORMATION: N6-tertiary-butyl-benzyl-dA

<400> SEQUENCE: 79
agtaagaata ggtgattttg gtctanctac at                                    32

<210> SEQ ID NO 80
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (31)..(31)
<223> OTHER INFORMATION: N6-tertiary-butyl-benzyl-dA

<400> SEQUENCE: 80
```
agtaagaata ggtgattttg gtctagctac at                                        32

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: N6-tertiary-butyl-benzyl-dA

<400> SEQUENCE: 81
aatgggtgat tttggtctag ctactgg                                              27

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: N6-tertiary-butyl-benzyl-dA
<220> FEATURE:
<221> NAME/KEY: modified_base
<222> LOCATION: (26)..(26)
<223> OTHER INFORMATION: Inosine

<400> SEQUENCE: 82
aatgggtgat tttggtctag ctatang                                              27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-tertiary-butyl-benzyl-dA

<400> SEQUENCE: 83
agtaggtgat tttggtctag ctatagg                                              27

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: N6-tertiary-butyl-benzyl-dA
<220> FEATURE:
<221> NAME/KEY: modified_base
<222> LOCATION: (26)..(26)
<223> OTHER INFORMATION: Inosine

<400> SEQUENCE: 84
aatgggtgat tttggtctag ctatanc                                              27

-continued

```
<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N4-tertiary-butyl-benzyl-dC
<220> FEATURE:
<221> NAME/KEY: modified_base
<222> LOCATION: (26)..(26)
<223> OTHER INFORMATION: Inosine

<400> SEQUENCE: 85
aatgggtgat tttggtctag ctactnc                                        27

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: N4-tertiary-butyl-benzyl-dC

<400> SEQUENCE: 86
aatgggtgat tttggtctag ctactgc                                        27

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtggaaaaat agcctcaatt cttacca                                        27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tagcctcaat tcttaccatc cacaaaa                                        27

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ctagtaactc agcagcatct cag                                            23

<210> SEQ ID NO 90
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ-2
<220> FEATURE:
<223> OTHER INFORMATION: 3'-Phosphate

<400> SEQUENCE: 90
cagacaactg ttcaaactga tggg                                            24

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ-2
<220> FEATURE:
<223> OTHER INFORMATION: 3'-Phosphate

<400> SEQUENCE: 91
cagtttgaac agttgtctgg atcca                                           25

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<223> OTHER INFORMATION: 3'-BHQ-2 Phosphate

<400> SEQUENCE: 92
tctcgatgga gtgggtcc                                                   18

<210> SEQ ID NO 93
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acatgaaagt attaagaggc tgagactcct ca                                   32

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gaagaaagcg aaaggagcgg gc                                              22

<210> SEQ ID NO 95
<211> LENGTH: 24
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 95
ggaacgaggg tagcaacggc taca                                            24

<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ-2
<220> FEATURE:
<223> OTHER INFORMATION: 3'-Phosphate

<400> SEQUENCE: 96
caaaaatgga ttggatc                                                    17

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ-2
<220> FEATURE:
<223> OTHER INFORMATION: 3'-Phosphate

<400> SEQUENCE: 97
tcttccacac aattaaacag catg                                            24

<210> SEQ ID NO 98
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ-2
<220> FEATURE:
<223> OTHER INFORMATION: 3'-Phosphate

<400> SEQUENCE: 98
ggaaagtggc atggtaa                                                    17

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-BHQ-2
<220> FEATURE:
<223> OTHER INFORMATION: 3'-Phosphate

<400> SEQUENCE: 99
agtatgtaat gtggtgacat t                                               21
```

SUPPRESSION OF NON-SPECIFIC AMPLIFICATION WITH HIGH-HOMOLOGY OLIGONUCLEOTIDES

SEQUENCE LISTING

The instant application contains a Sequence Listing which has been submitted in ASCII format via EFS-Web and is hereby incorporated by reference in its entirety. Said ASCII copy, created on Nov. 20, 2012, is named 30622US1.txt and is 27 bytes in size.

BACKGROUND OF THE INVENTION

Amplification of nucleic acids by polymerase chain reaction (PCR) has many applications in biomedical research, diagnostics and biotechnology. The unique specificity of PCR enables selective amplification of a particular nucleic acid sequence in the presence of overwhelming amount of other sequences. Furthermore, PCR can distinguish a target sequence from another sequence that is different by as little as a single base-pair. For example, allele-specific PCR (AS-PCR) is capable of detecting small alterations in DNA and even single nucleotide mutations in the presence of the wild-type, non-mutant DNA (U.S. Pat. No. 6,627,402). In an allele-specific PCR assay, at least one primer is allele-specific, i.e. designed to preferentially match the target sequence (a specific variant of the sequence), but contains discriminating mismatches with non-target sequences (other variants of the sequence). Ideally, primer extension occurs only when the allele-specific primer is hybridized to the target sequence. In a successful allele-specific PCR, the target variant of the nucleic acid is amplified, while the other non-target variants are not, at least not to a detectable level. Unfortunately, with many targets, this ideal is not achievable. It is common that in later cycles of PCR, amplification of the non-target variants of the sequence also becomes detectable. This phenomenon is called "breakthrough amplification." Even though the AS-PCR primers are perfectly complementary (or at least, share the greater degree of complementarity) with the target sequence and are mismatched (or have more mismatches) with non-target sequences, often amplification of the non-target sequences cannot be completely avoided.

Breakthrough amplification is of special concern in assays where the sample contains small amounts of the target sequence and large amounts of the non-target sequence. For example, in an assay targeting a somatic mutation in a tumor, only a fraction of cells from the patient's sample are tumor cells. A fraction of tumor cells may contain mutations indicating susceptibility to a particular anti-tumor drug (mutations described in U.S. Pat. Nos. 7,294,468 and 7,960,118). In such a sample, a small number of the target (mutant) sequences are mixed with a large number of non-target (non-mutant) sequences. Breakthrough amplification of the non-mutant sequence would produce a false-positive result, falsely indicating the presence of a mutation and misdirecting the patient's therapy. If the specificity of the assay is limited by the breakthrough amplification, so is the clinical utility of the assay.

Various means of preventing or reducing non-specific amplification have been proposed (for example, chemical modifications that affect the specificity of amplification primers, see U.S. Pat. No. 6,011,611; using a blocker oligonucleotide, see U.S. Application Pub. No. 200953720). However, these methods are not always successful in entirely eliminating the breakthrough amplification. Accordingly, there is a need for alternative methods of preventing or minimizing breakthrough amplification in a nucleic acid amplification reaction.

SUMMARY OF THE INVENTION

In one embodiment, the invention is a suppressor oligonucleotide for use in a nucleic acid amplification reaction, having a sequence comprising at least one region of homology with at least 75% identity to multiple sites in the genome of a target organism.

In another embodiment, the invention is a method of designing a suppressor oligonucleotide for use in a nucleic acid amplification reaction, comprising using sequence alignment algorithms to select an oligonucleotide having a sequence comprising at least one region of homology with at least 75% identity to multiple sites in the genome of a target organism.

In yet another embodiment, the invention is a method of reducing amplification of a non-target nucleic acid template in a nucleic acid amplification reaction, comprising performing the amplification reaction in the presence of a suppressor oligonucleotide having a sequence comprising at least one region of homology with at least 75% identity to multiple sites in the genome of a target organism.

In yet another embodiment, the invention is a kit for performing an amplification reaction with reduced amplification of the non-target sequences, comprising a suppressor oligonucleotide having a sequence comprising at least one region of homology with at least 75% identity to multiple sites in the genome of a target organism.

In yet another embodiment, the invention is a reaction mixture for performing an amplification reaction with reduced amplification of the non-target sequences, comprising a suppressor oligonucleotide having a sequence comprising at least one region of homology with at least 75% identity to multiple sites in the genome of a target organism.

In yet another embodiment, the invention is the use of a suppressor oligonucleotide having a sequence comprising at least one region of homology with at least 75% identity to multiple sites in the genome of a target organism, in a nucleic acid amplification reaction to reduce non-specific amplification.

BRIEF DESCRIPTION OF THE DRAWINGS

FIG. 1 shows amplification of exon 2 (including codon 12) of the human NRAS gene by allele-specific PCR with breakthrough suppression by the suppressing oligonucleotide, also used as one of the primers.

FIG. 2 shows amplification of exon 3 (including codon 61) of the human NRAS gene by allele-specific PCR with breakthrough suppression by the suppressing oligonucleotide that is not complementary to the target sequence.

FIG. 3 shows amplification of the human PI3KCA gene by allele-specific PCR with breakthrough suppression by the suppressing oligonucleotide that is not complementary to the target sequence.

FIG. 4 shows amplification of the human BRAF gene (including codons 469 and 600) by allele-specific PCR with breakthrough amplification suppression by the suppressing oligonucleotide that is not complementary to the target sequence.

FIG. 5 shows amplification of exons 2 and 3 of the human NRAS gene by allele-specific PCR with breakthrough suppression by simultaneous linear amplification of the M13 target.

FIG. 6 shows amplification of exon 2 of the human NRAS gene by allele-specific PCR with breakthrough suppression by suppressing oligonucleotides with varying degrees of homology to the target genome.

FIG. 8 shows an example of selecting suppressing oligonucleotides from the region of interest in exon 2 of human NRAS gene.

DETAILED DESCRIPTION OF THE INVENTION

Figure 1A:
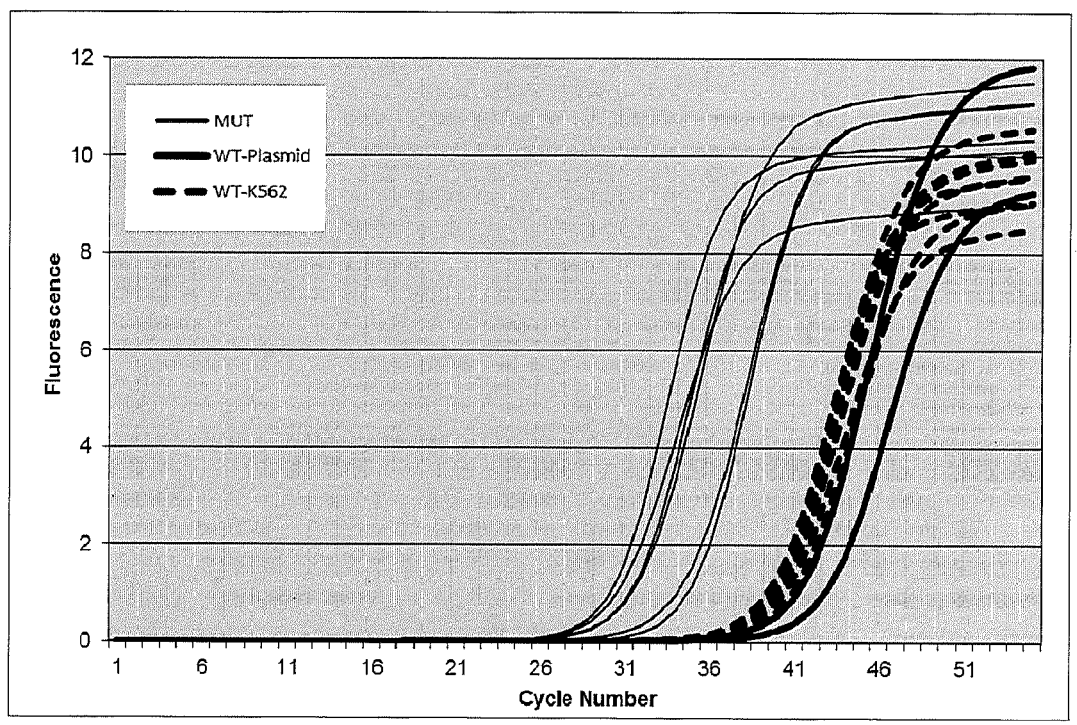
FIG. 1A shows unsuppressed breakthrough amplification (dashed line)

To facilitate the understanding of this disclosure, the following definitions of the terms used herein are provided.

The term "allele-specific primer" or "AS primer" refers to a primer that may hybridize to more than one variant of the target sequence, but is capable of discriminating among variants of the target sequence, such that efficient extension of the primer by the nucleic acid polymerase under suitable conditions occurs only upon hybridization of the primer to one particular variant. With other variants of the target sequence, the extension is less efficient or inefficient.

The term "amplicon" refers to a nucleic acid formed as a product of a polymerase chain reaction.

The term "common primer" refers to the second primer in the pair of primers that includes an allele-specific primer. The common primer is not allele-specific, i.e. does not discriminate between the variants of the target sequence between which the allele-specific primer discriminates.

The terms "complementary" or "complementarity" are used in reference to antiparallel strands of polynucleotides related by the Watson-Crick base-pairing rules. Complementary nucleic acid strands are capable of forming duplexes under standard hybridization conditions. The terms "perfectly complementary" or "100% complementary" refer to complementary sequences that have Watson-Crick pairing of all the bases between the antiparallel strands, i.e. there are no mismatches between any two bases in the polynucleotide duplex. The terms "partially complementary" or "incompletely complementary" refer to any alignment of bases between antiparallel polynucleotide strands that is less than 100% perfect (e.g., there exists at least one mismatch or unmatched base in the polynucleotide duplex). A smaller nucleic acid strand (e.g. an oligonucleotide) may be complementary to a region (site) in a larger nucleic acid, e.g. a gene or a genome. Under standard hybridization conditions, duplexes are formed between antiparallel strands even in the absence of perfect complementarity. However, duplexes between partially complementary strands are generally less stable than the duplexes between perfectly complementary strands.

A "growth curve" in the context of a nucleic acid amplification assay is a graph of a function, where an independent variable is the number of amplification cycles and a dependent variable is an amplification-dependent measurable parameter measured at each cycle of amplification. Typically, the amplification-dependent measurable parameter is the amount of fluorescence emitted by the probe upon hybridization, or upon the hydrolysis of the probe by the nuclease activity of the nucleic acid polymerase, see Holland et al., (1991) Proc. Natl. Acad. Sci. 88:7276-7280 and U.S. Pat. No. 5,210,015. In a typical polymerase chain reaction, a growth curve comprises a segment of exponential growth followed by a plateau. A growth curve is typically characterized by a "cycles to threshold" value or "$C_t$" value, which is a number of cycles where a predetermined magnitude of the measurable parameter is achieved. A lower or "earlier" $C_t$ value represents more rapid amplification, while the higher or "later" $C_t$ value represents slower amplification.

The terms "homology" and "regions of homology" refer to regions (sites) where two nucleic acids share at least partial complementarity. A region of homology may span only a portion of the sequences. For example, only a portion of an oligonucleotide may be homologous to a site in the genome. Different portions of the oligonucleotide may be homologous to several distinct sites in the genome, while an entire oligonucleotide may be homologous to yet another site in the genome. As with any partially complementary nucleic acid sequences, a region of homology may contain one or more mismatches and gaps when the two sequences are aligned. A smaller nucleic acid strand (e.g. an oligonucleotide) may be homologous to a region (site) in a larger nucleic acid, e.g. a gene or a genome. The term "degree of homology" between two sequences refers to the extent of identity between the sequences. The extent of identity is commonly expressed as a ratio of mismatched nucleotides in the homologous region to the total number of nucleotides, expressed in percentage. For example, a 20-base oligonucleotide that hybridizes to a homologous region (site) in the target genome with two mismatches is said to have 90% identity to that region. The term "degree of homology to the target genome" is a measure of the number and percent identity of regions of homology to the oligonucleotide present in the target genome. An oligonucleotide with high degree of homology has many regions of homology with high percentage of identity throughout the target genome, while an oligonucleotide with low degree of homology region would have fewer regions of homology with low percentage of identity in the target genome.

The terms "hybridized" and "hybridization" refer to the base-pairing interaction between two at least partially complementary (as defined herein) nucleic acid strands which results in formation of a duplex. It is not a requirement that two nucleic acids have 100% complementarity over their full length to achieve hybridization. A smaller nucleic acid strand (e.g. an oligonucleotide) may hybridize to a region (site) in a larger nucleic acid, e.g. a gene or a genome.

The term "multiple regions of homology" in relation to suppressor oligonucleotides homologous to regions of a target genome is used to describe the number of such regions in the target genome that is sufficient to support the suppressing property of the oligonucleotide. In general, "multiple" means more than one, for example, 2, 3, 20, 30, 200, 300, 2000, 3000, etc., and any whole number in between. However, a sufficient number varies depending on the complexity of the target genome, i.e. for less complex genomes, a smaller number may be sufficient for the suppression phenomenon to occur, while for more complex genomes, a greater number would be required.

The terms "nucleic acid," "oligonucleotide" and "polynucleotide" are used interchangeably to describe polymers of deoxyribo- (or ribo-) nucleic acid, including primers, probes, genomic DNA or RNA of various organisms and fragments of genomic DNA or RNA as well as other genetic elements, e.g. plasmids, cosmids, etc. The terms are not limited by length and are generic to polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded nucleic acids. Nucleic acids can comprise naturally occurring phosphodiester linkages or modified linkages including, but not limited to thioesther linkages. Likewise, nucleic acids can comprise the five biologically occurring bases (adenine, guanine, thymine, cytosine and uracil) or other modified, non-standard, or derivatized base moieties.

The terms "polynucleotide" and "oligonucleotide" are used interchangeably. "Oligonucleotide" is a term sometimes used to describe a shorter polynucleotide. An oligonucleotide may be comprised of at least 6 nucleotides and up to 100 nucleotides.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. A perfect complementarity is not required for the primer extension to occur. However, a primer with perfect complementarity (especially near the 3'-terminus) will be extended more efficiently than a primer with mismatches, especially mismatches at or near the 3'-terminus.

The term "probe" refers to an oligonucleotide which hybridizes with a sequence in the target nucleic acid and may be detectably labeled. The probe can have modifications, such as a 3'-terminus modification that makes the probe non-extendable by nucleic acid polymerases; and one or more chromophores. An oligonucleotide with the same sequence may serve as a primer in one assay and a probe in a different assay.

The term "region of interest" refers to a region of the target genome from which the suppressor oligonucleotide is to be designed.

The term "sample" refers to any composition containing or presumed to contain nucleic acid. This includes a sample of tissue or fluid isolated from an individual. For example, skin, plasma, serum, spinal fluid, lymph fluid, synovial fluid, urine, tears, blood cells, organs and tumors, and also samples of in vitro cultures established from cells taken from an individual, including the formalin-fixed paraffin embedded tissues (FF-PET) and nucleic acids isolated therefrom.

The term "suppressor oligonucleotide" refers to an oligonucleotide that, when present in the PCR mixture, suppresses or detectably reduces amplification of any non-target sequences. In some instances, the suppressor oligonucleotide detectably reduces exponential amplification of the non-target sequence in allele-specific PCR. The suppressor oligonucleotide may optionally, have additional functions, including serving as a primer for amplification of the target sequence.

A "template" or "target" refers to a nucleic acid which is to be amplified, detected or both. The target or template is a sequence to which a primer or a probe can hybridize. Template nucleic acids can be derived from essentially any source, including microorganisms, complex biological mixtures, tissues, bodily fluids, sera, preserved biological samples, environmental isolates, in vitro preparations or the like. The template or target may constitute all or a portion of a nucleic acid molecule.

The term "target organism" refers to an organism whose nucleic acid sample is being analyzed. The genome of the target organism is referred to as "target genome."

The term "target sequence" refers to the sequence of the target organism of which amplification is desired. The term "non-target sequence" refers to another sequence of which amplification is not desired and is to be avoided. In the context of allele-specific PCR, the non-target sequence of concern is often a very similar variant of the target sequence. Although it is not desired, the non-target sequence is sometimes amplified by allele-specific PCR along with the target sequence, but with lower efficiency.

Polymerase chain reaction (PCR) is capable of specifically amplifying a target nucleic acid sequence present amidst a much larger number of other sequences. Allele-specific PCR (AS-PCR) is a method capable of distinguishing between sequences that differ by as little as a single nucleotide. The sensitivity and specificity of PCR and AS-PCR is such that the target variant of the nucleic acid can be selectively amplified even in the presence of much larger amounts of non-target variants and unrelated sequences. Ideally, the non-target nucleic acids are never amplified to a detectable level. However, sensitivity of PCR and AS-PCR assays is challenged by a phenomenon called "breakthrough amplification," which is detectable amplification of the non-target nucleic acid sequences during the later cycles of PCR.

Figure 1B:
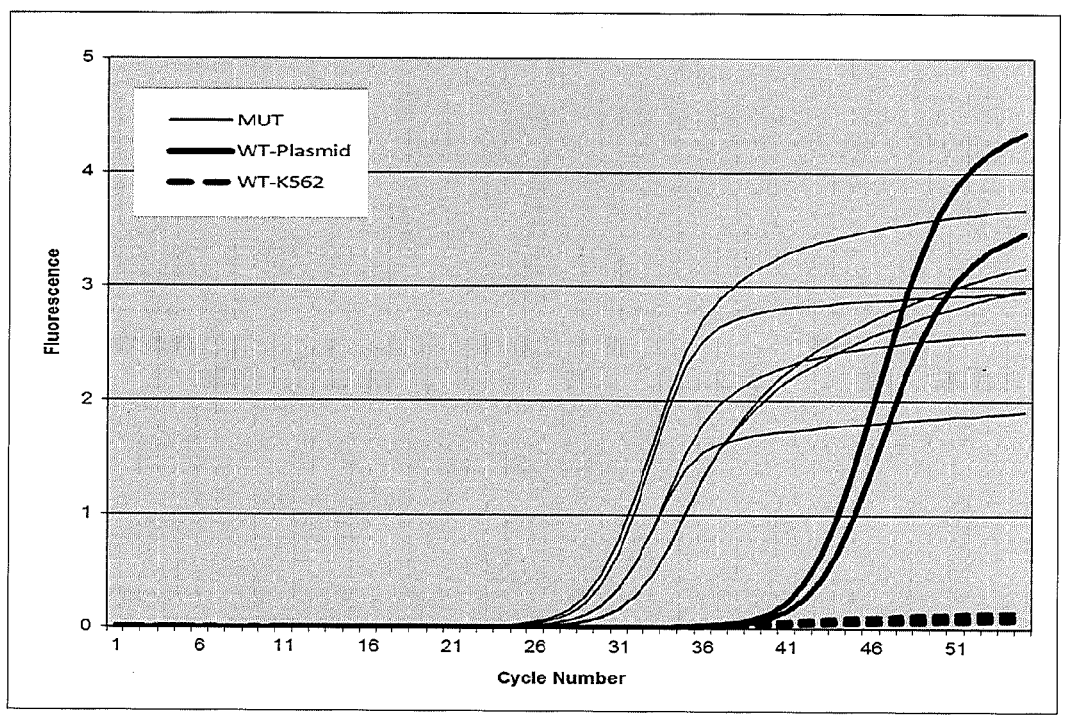
FIG. 1B shows suppression of the non-target sequence amplification.

In conducting allele-specific PCR, the inventors discovered that certain oligonucleotides (initially used as primers) significantly reduce breakthrough amplification when present in AS-PCR assays (Example 1, FIG. 1). When these suppressor oligonucleotides were further investigated, it was discovered that most surprisingly, the oligonucleotides exert the same effect on unrelated targets, i.e. targets that have no regions of complementarity with the suppressor oligonucleotides, (Example 2, FIG. 2, Example 3, FIG. 3, and Example 4, FIG. 4). Accordingly, the inventors devised methods of designing and using such oligonucleotides for improving PCR and AS-PCR assays.

While not wishing to be bound by a particular theory, the inventors hypothesize that one of the mechanisms of breakthrough suppression may be sequestering PCR reagents in the later cycles of amplification when the breakthrough amplification usually occurs. In the later cycles of PCR, amplification of the target sequence ceases (the plateau is reached), in part because re-annealing of double-stranded amplicons is kinetically favored over annealing of primers to single strands of denatured amplicons. At that stage, excess primers become available for the less specific (and thus less efficient) breakthrough amplification that involves extension of a mismatched primer hybridized to the non-target sequence. However, thermodynamic parameters of the mismatched primer extension are unfavorable. Accordingly, the mismatched primer extension is greatly affected by the depletion or sequestering of components such as nucleotides and nucleic acid polymerase. The properties of the suppressor oligonucleotide allow for linear primer extension elsewhere in the genome and (optionally) for exponential generation of additional amplicons elsewhere in the genome. These extraneous reactions, although arguably not very efficient themselves, sequester critical reagents and inhibit breakthrough amplification requiring these reagents.

Figure 5A:
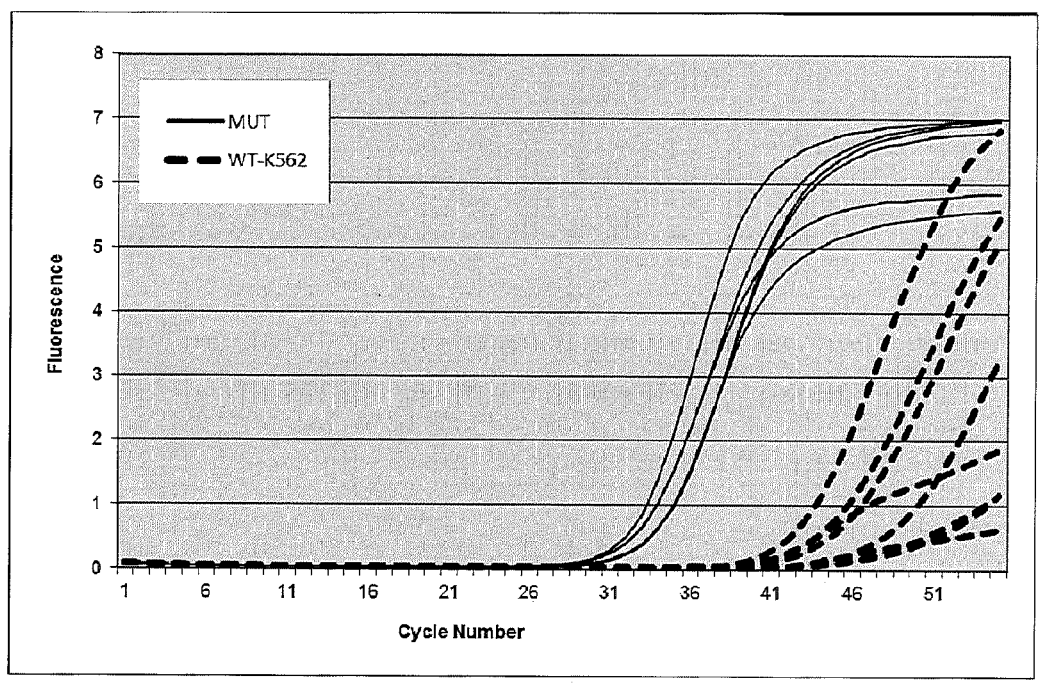
FIG. 5A shows breakthrough amplification of the non-target (wild-type) NRAS sequence in the presence of a primer pair consisting of an allele-specific primer matched to one of the mutations in codon 61 and a common primer.
Figure 5B:
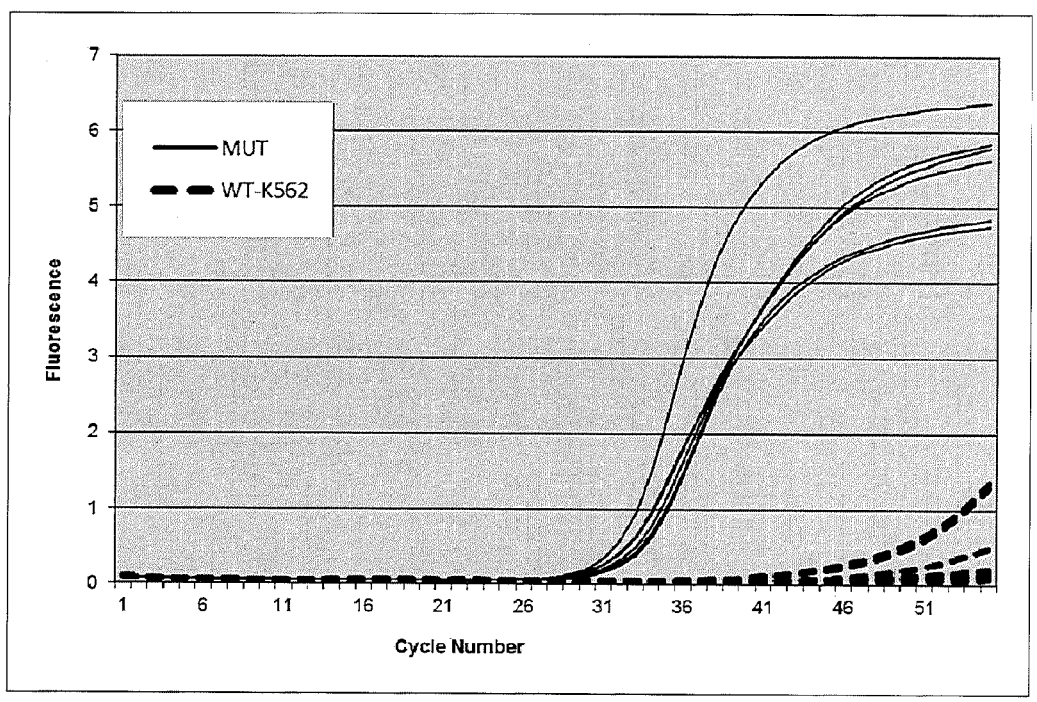
FIG. 5B shows suppression of breakthrough amplification of the non-target (wild-type) NRAS sequence by M13 DNA and three primers capable of linear amplification of the M13 DNA.
Figure 5C:
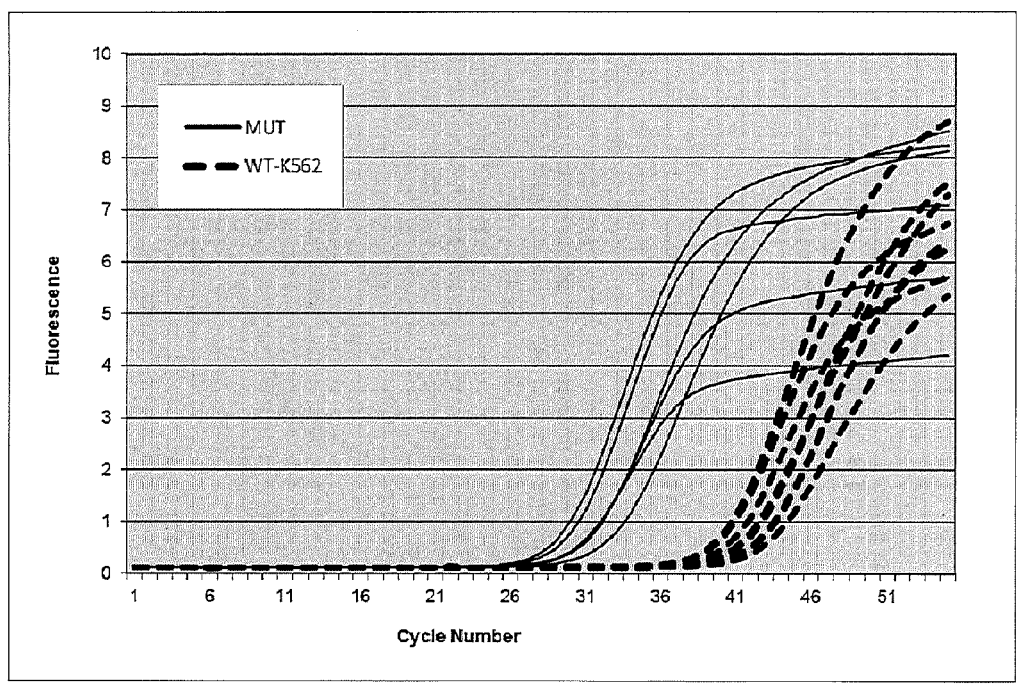
FIG. 5C shows breakthrough amplification of the non-target (wild-type) NRAS sequence in the presence of an allele-specific primer matched to one of the mutations in codon 12 and a common primer.
Figure 5D:
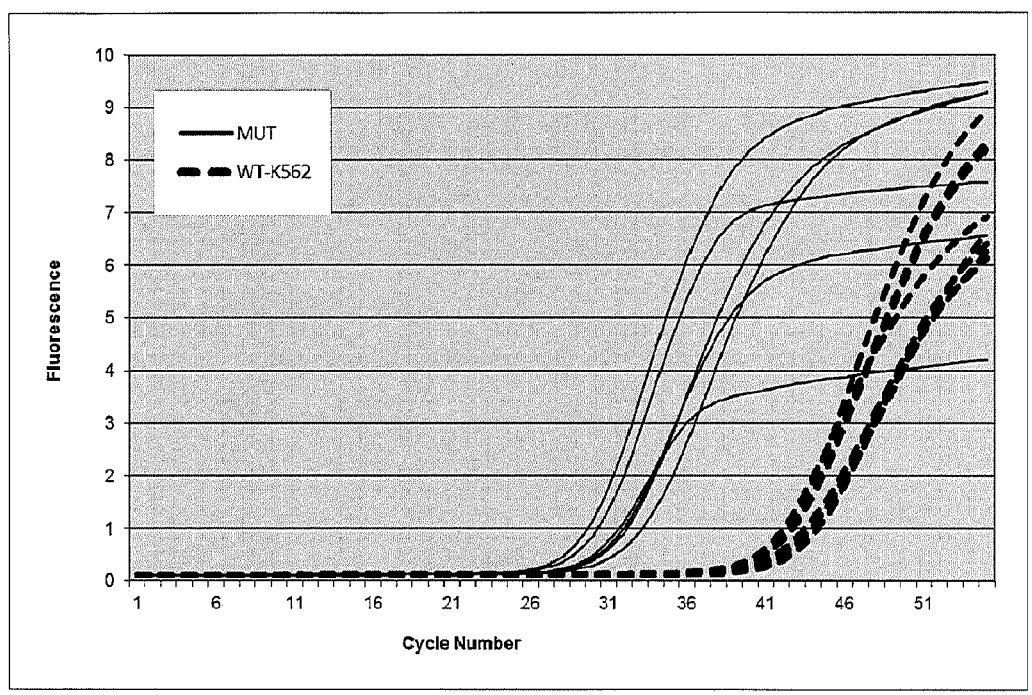
FIG. 5D shows suppression of breakthrough amplification of the non-target (wild-type) NRAS sequence M13 DNA and three primers capable of linear amplification of the M13 DNA.

To test this hypothesis, the inventors conducted an experiment described in Example 5. In that example, an AS-PCR assay known for its breakthrough amplification (FIG. 5A) was conducted in the presence of an engineered primer/target combination capable of priming multiple linear extension reactions. The multiple linear extension reactions were predicted to generate some of the depletion effect and suppress the breakthrough amplification. Indeed, some suppression of the breakthrough amplification was observed (FIG. 5B).

In one embodiment, the invention is a suppressor oligonucleotide for suppressing amplification of non-target sequences in an amplification reaction, for example, PCR or allele-specific PCR (AS-PCR). The suppressor oligonucleotide is homologous to multiple sites in the genome of the target organism. These sites in the target genome comprise regions of homology with the suppressor oligonucleotide. In some embodiments, the regions of homology between the suppressor oligonucleotide and the target genome have at least 75% identity. In some embodiments, the regions of homology are at least 15 base pairs long. However, it is understood that for certain sequences (for example, GC-rich sequences) shorter regions of homology or regions with less than 75% identity may also offer satisfactory results. Generally, the higher the identity in each of the regions of homology, the better the suppressing effect as demonstrated in Example 6, FIG. 6. In yet other embodiments, the region of homology spans the 3'-end of the suppressor oligonucleotide. In yet other embodiments, within the last four base pairs at the 3'-end of the oligonucleotide, the region of homology contains no more than 2 mismatches.

It is desirable that the suppressor oligonucleotide cause minimal interference with amplification and detection of the target sequence. If a suppressor oligonucleotide is capable of generating additional (non-target) amplicons, these additional amplicons may be detected, and thus interfere with detection of the target sequence. Generation of these amplicons by the suppressor oligonucleotide is preferably avoided. In variations of this embodiment, the suppressor oligonucleotide possesses an additional property: it is not capable of generating additional amplicons. A PCR amplicon is generated in an exponential fashion only when both forward and reverse primers are present. Therefore an oligonucleotide is capable of priming exponential synthesis of an amplicon if it is paired with another oligonucleotide (including itself) that is capable of hybridizing to a sequence on the opposite strand of the same nucleic acid, said sequence located no more than approximately 1000 base pairs away from the site of the hybridization of the first oligonucleotide. It is understood that in some instances, for example when a highly processive nucleic acid polymerase is used (see e.g. U.S. Pat. No. 7,855,055), non-target amplicons longer than 1000 base pairs may also be generated and interfere with amplification and detection of the target nucleic acid. Accordingly, when a highly processive polymerase is used, a potential suppressor oligonucleotide may be excluded based on an upper limit higher than 1000 base pairs. In that case, more potential suppressor oligonucleotides would be excluded. On the other hand, with fragmented nucleic acid (for example, nucleic acid isolated from formalin-fixed paraffin-embedded tissues, FFPET), longer amplicons are not possible and a potential suppressor oligonucleotide may be excluded based on a limit shorter than 1000 base pairs. In that case, fewer potential suppressor oligonucleotides would be excluded. According to the present invention, in some embodiments, an oligonucleotide is not used as a suppressor oligonucleotide if it has at least two regions of homology located on the opposite strands of the target genome, said regions having at least 75% identity between the oligonucleotide and the target genome sequence, wherein said regions of homology are separated by fewer than approximately 1000 base pairs.

A suppressor oligonucleotide can be prepared by any suitable method of preparing an oligonucleotide, usually chemical synthesis using commercially available reagents and instruments. Alternatively, an oligonucleotide can be purchased through commercial sources. Methods of synthesizing oligonucleotides are well known in the art (see, Narang et al., *Meth. Enzymol.* 68:90-99, 1979; Brown et al., *Meth. Enzymol.* 68:109-151, 1979; Beaucage et al., *Tetrahedron Lett.* 22:1859-1862, 1981; or U.S. Pat. No. 4,458,066).

In variations of this embodiment, the invention comprises suppressor oligonucleotides of SEQ ID NOs: 1-5 (Table 1).

In another embodiment, the invention is a method of designing a suppressor oligonucleotide for suppressing amplification of non-target sequences in amplification reaction, for example, PCR or allele-specific PCR (AS-PCR). The method of designing suppressor oligonucleotides of the present invention relies on sequence alignment algorithms. In some embodiments, oligonucleotide design method of the present invention uses sequence alignment software. Such software is currently widely available and in many instances, is accessible to the public free of charge. For example, National Institutes of Health has made available free of charge through its website the BLAST® (Basic Local Alignment Search Tool) software package. The invention is not limited to the use of BLAST®, but rather BLAST® is merely an example of a suitable software package. Other examples of pairwise sequence alignment software include ACANA (Huang et al. (2006) *Accurate anchoring alignment of divergent sequences*. Bioinformatics 22:29-34), Bioconductor (open-source software freely distributed by the Fred Hutchinson Cancer Research Center), FEAST (software package distributed free of charge by the University of Waterloo, Canada), FASTA (software package distributed free of charge by the University of Virginia), REPuter (Kurtz et al. (2001) *REPuter: The Manifold Applications of Repeat Analysis on a Genomic Scale*, Nucleic Acids Res., 29(22):4633-4642), SWIFT BALSAM (BAsic fiLter for Semigobal non-gapped AlignMent search) (Rasmussen et al. (2006) *Efficient q-Gram*

*Filters for Finding All epsilon-Matches over a Given Length*, J. Comp. Biol. 13(2), 296-308).

In one embodiment, the method of the present invention comprises the use of sequence alignment algorithms to select an oligonucleotide characterized by having multiple regions of homology with the target genome. In some embodiments, the method uses sequence alignment algorithms to select an oligonucleotide where the regions of homology between the suppressor and the target genome have at least 75% identity. In some embodiments, the method uses sequence alignment algorithms to select an oligonucleotide where the regions of homology are at least 15 base pairs long. In yet other embodiments, the method uses sequence alignment algorithms to select an oligonucleotide where the regions of homology span the 3'-end of the oligonucleotide. In yet other embodiments, the method uses sequence alignment algorithms to select an oligonucleotide where within the last four base pairs at the 3'-end of the oligonucleotide, the region of homology contains no more than 2 mismatches.

In variations of this embodiment, the method of the present invention comprises the use of sequence alignment algorithms to exclude an oligonucleotide from use as a suppressor oligonucleotide if the oligonucleotide has at least two regions of homology located on the opposite strands of the target genome, said regions having at least 75% identity between the oligonucleotide and the target genome sequence, wherein said regions of homology are separated by fewer than approximately 1000 base pairs.

In some embodiments of the invention, the suppressor oligonucleotide is derived from a region of interest selected by the user. The region of interest may contain or be adjacent to the target sequence, or may be an unrelated region of the genome. There is no limitation on the size of the region of interest, although generally a larger region may yield more options for the design of the suppressor oligonucleotides. In general, the region of interest should possess some of the characteristics desired in the suppressor oligonucleotides. In some embodiments of the method, the region of interest comprises multiple regions of homology with the target genome that have at least 75% identity and are at least 15 nucleotides long.

In one embodiment, the method of the present invention comprises the following steps performed with the use of sequence alignment algorithms:

(a) identify one or more regions of interest;
(b) conduct a search of the target genome sequence using the regions of interest as a query to identify regions of homology between the region of interest and the target genome;
(c) select sections of the region of interest having the most regions of homology to the target genome;
(d) design one or more oligonucleotides in the sections selected in step (c);
(e) conduct a search of the target genome with the oligonucleotides designed in step (d) to identify the oligonucleotides with the maximum number of regions of homology to the target genome meeting one or both of the following criteria: at least 75% identity and no more than 2 mismatches present in the 3'-terminal region of the oligonucleotide;
(f) optionally, conduct a search of the target genome with the oligonucleotides designed in step (d) to identify and exclude the oligonucleotides having at least two regions of homology located on the opposing strands of the target genome sequence that are separated by fewer than approximately 1000 base pairs.

In general, the region of interest and the oligonucleotide with the most regions of homology identified in step (e), and optionally, selected as not capable of generating a non-target amplicon (f) are to be selected. It is however understood, that an excessive number of regions of homology may be detrimental to the assay as a whole. For example, an oligonucleotide homologous to a highly repetitive element in the target genome will initiate an excessive number of primer extensions that will overwhelm the reaction. See e.g. Kazazian, H (2004) *Mobile Elements: Drivers of Genome Evolution*, Science 303 (5664): 1626-1632 (Alu repetitive element constitutes 11% of the human genome, i.e. occurs about $3\times10^8$ times throughout the genome).

Figure 7:
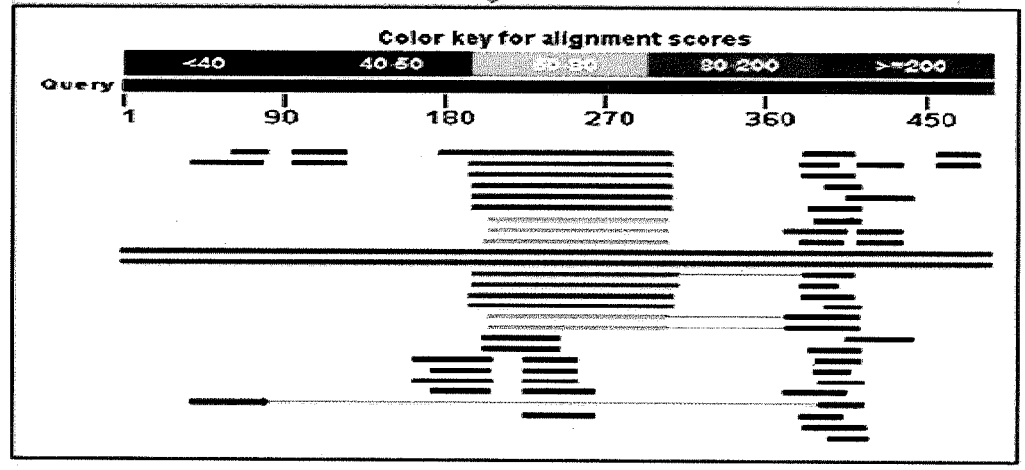
FIG. 7 shows results of a BLAST® search for the regions of interest in exon 2 of human NRAS gene for the design of suppressing oligonucleotides.

Example 6 demonstrates application of the method. FIG. 7 is an illustration of steps (a) through (c) performed using BLAST®. FIG. 8 is an illustration of steps (d) through (e) performed using BLAST®.

TABLE 1

Suppressor oligonucleotides

| SEQ ID NO: | Sequence 5'-3' |
|---|---|
| SEQ ID NO: 1 | CTACCACTGGGCCTCACCT |
| SEQ ID NO: 2 | CAGGATCAGGTCAGCGGGCT |
| SEQ ID NO: 3 | AGACAGGATCAGGTCAGCGGG |
| SEQ ID NO: 4 | CAGGTCAGCGGGCTACCACT |
| SEQ ID NO: 5 | ACAAGTGAGAGACAGGATCAGGTC |

For successful extension of a primer, the primer needs to have at least partial complementarity to the target sequence. Generally, complementarity at the 3'-end of the primer is more critical than complementarity at the 5'-end of the primer. (Innis et al. Eds. *PCR Protocols*, (1990) Academic Press, Chapter 1, pp. 9-11). Therefore the present invention encompasses the oligonucleotides disclosed in Table 1, as well as variants of these oligonucleotides with 5'-end variations.

In one embodiment, the invention is a method of suppressing amplification of a non-target sequence in an amplification reaction, for example, PCR or allele-specific PCR (AS-PCR), comprising conducting the AS-PCR in the presence of a suppressor oligonucleotide that is homologous to multiple sites in the genome sequence of the target organism. In some embodiments, the regions of homology between the suppressor oligonucleotide and the target genome have at least 75% identity. In some embodiments, the regions of homology are at least 15 base pairs long. In yet other embodiments, the region of homology spans the 3'-end of the suppressor oligonucleotide. In yet other embodiments, within the last four base pairs of the 3'-end of the oligonucleotide, the region of homology contains no more than 2 mismatches. In yet other embodiments, an oligonucleotide is not used as a suppressor oligonucleotide if it has at least two regions of homology located on the opposite strands of the target genome, said regions of homology having at least 75% identity between the oligonucleotide and the target genome sequence, wherein said regions of homology are separated by fewer than approximately 1000 base pairs.

The method of the present invention is applicable to traditional PCR as well as allele-specific PCR. Allele-specific PCR is a variation of PCR where the primers are designed to amplify the target sequence but avoid amplification of another, closely related sequence. Allele-specific PCR is described e.g. in U.S. Pat. No. 6,627,402. In allele-specific PCR, at least one of the primers is the discriminating primer having a sequence complementary to the target sequence, but having mismatches with the non-target sequence. Typically, the discriminating nucleotide in the primer, i.e. the nucleotide matching only the target sequence, is the 3'-terminal nucleotide. In cases where the primer is not perfectly complementary to the target sequence, it still comprises a greater degree of complementarity to the target sequence compared to the non-target sequence. Design of allele-specific primers and general methods of optimizing the primers for nucleic acid amplification have been described, for example, in *PCR Protocols: A Guide to Methods and Applications*, Innis et al., eds., (1990) Academic Press.

Typically, primers are synthetic oligonucleotides, composed of A, C, G and T nucleotides. However, unconventional base nucleotides, not normally found in nucleic acids, can also be used. For example, certain modified bases are known to increase specificity of amplification, see U.S. Pat. No. 6,001,011. Innis et al. (supra) also contains guidance on selecting nucleic acid polymerases for use in PCR. Exemplary thermostable DNA polymerases include those from *Thermus thermophilus, Thermus caldophilus, Thermus* sp. ZO5 (see, e.g., U.S. Pat. No. 5,674,738), *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Thermotoga maritima, Thermotoga neapolitana* and *Thermosipho africanus*.

Detection of the amplification products may be accomplished by any method known in the art. These detection methods include the use of labeled primers and probes as well as various nucleic acid-binding dyes. The means of detection may be specific to one variant of the target sequence, or may be generic to all variants of the target sequence or even to all double stranded DNA. The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of having a labeled primer. After or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In some embodiments, the presence of the amplification product may be detected in a homogeneous assay, i.e. an assay where the nascent product is detected during the cycles of amplification, and no post-amplification handling is required. A homogeneous amplification assay using a nuclease probe has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ one or more fluorescent probes where hybridization of the probes to the extension product results in enzymatic digestion of the probe and detection of the resulting fluorescence (TaqMan™ probe method, Holland et al. (1991) P.N.A.S. USA 88:7276-7280). Other methods use two probes labeled with two interacting fluorophores. The examples of such probes include "molecular beacon" probes (Tyagi et al., (1996) *Nat. Biotechnol.*, 14:303-308) or fluorescently labeled nuclease probes (Livak et al., (1995) *PCR Meth. Appl.*, 4:357-362).

In a homogeneous assay, the reaction is characterized by a growth curve showing the increase in fluorescence of a probe with each cycle of PCR. See Holland et al., (supra) and U.S. Pat. No. 5,210,015. Each growth curve is characterized by a "cycles to threshold" value or "$C_t$" value. A lower $C_t$ value represents more rapid completion of amplification, while the higher $C_t$ value represents slower completion of amplification. A lower $C_t$ value may also represent a greater initial input of the target nucleic acid, while a higher $C_t$ value may represent a smaller initial input. In the case of allele-specific PCR however, the lower $C_t$ value represents efficient amplification. During breakthrough amplification, the non-target sequence yields a very high $C_t$ value despite the large amount of the non-target sequence present. The high $C_t$ value reflects very inefficient amplification of the non-target nucleic acid.

In yet another embodiment, the invention is a kit containing reagents necessary for performing an amplification reaction, for example PCR or AS-PCR, with reduced amplification of non-target sequences. The reagents comprise one or more allele-specific primers, one or more corresponding common primers and optionally, one or more probes; and a suppressor oligonucleotide characterized by having multiple regions of homology with the target genome. In some embodiments, the regions of homology have one or more of the following properties: at least 75% identity between the suppressor oligonucleotide and the target genome sequence; at least 15 base pairs long; span the 3'-end of the suppressor oligonucleotide; and within the last four base pairs at the 3'-end of the oligonucleotide, the regions of homology contains no more than 2 mismatches. In yet other embodiments, an oligonucleotide is not included in the kit as a suppressor oligonucleotide if it has at least two regions of homology located on the opposite strands of the target genome, said regions of homology having at least 75% identity between the oligonucleotide and the target genome sequence, wherein said regions of homology are separated by fewer than approximately 1000 base pairs.

The kit may further comprise reagents necessary for the performance of an amplification and detection assay, such as nucleoside triphosphates, nucleic acid polymerase and buffers necessary for the function of the polymerase. In some embodiments, the probe is detectably labeled. In such embodiments, the kit may comprise reagents for detecting the label. Optionally, the kit may also contain reagents that enhance the performance of the PCR, including dUTP and uracil-N-glycosylase (UNG) to reduce contamination, and betaine to improve specificity.

In yet another embodiment, the invention is a reaction mixture for performing an amplification reaction, for example, PCR or allele-specific PCR, with reduced amplification of non-target sequences. The mixture comprises one or more allele-specific primers, one or more corresponding common primers and optionally, one or more probes; and a suppressor oligonucleotide characterized by having multiple regions of homology with the target genome. In some embodiments, the regions of homology have one or more of the following properties: at least 75% identity between the suppressor oligonucleotide and the target genome sequence; at least 15 base pairs long; span the 3'-end of the suppressor oligonucleotide; and within the last four base pairs of the 3'-end of the oligonucleotide, the region of homology contains no more than 2 mismatches. In yet other embodiments, an oligonucleotide is not included in the reaction mixture as a suppressor oligonucleotide if it has at least two regions of homology located on the opposite strands of the target genome, said regions of homology having at least 75% identity between the oligonucleotide and the target genome sequence, wherein said regions of homology are separated by fewer than approximately 1000 base pairs. The reaction mixture may further comprise reagents such as nucleoside triphosphates, nucleic acid polymerase and buffers necessary for the function of the polymerase.

EXAMPLES

Example 1

Suppression of Breakthrough Amplification by a PCR Primer

In this example, suppression of breakthrough amplification was observed in an AS-PCR targeting mutations in codon 12 of the human NRAS gene. The primers and probes used in Example 1 are shown in Table 2. An upstream primer selected from among SEQ ID NOs: 6-23 is matched to one of the mutations 35G>C, 34G>T, 35G>A, 34G>C, 34G>A, and 35G>T corresponding to amino acid changes G12A, G12C, G12D, G12R, G12S, and G12V in exon 2 of the human NRAS gene and is mismatched with the wild-type sequence. A downstream primer selected from SEQ ID NOs: 24-26 is common between the mutant and wild-type sequences of exon 2 in the human NRAS gene and the detection probe is selected from SEQ ID NOs: 27-29.

The standard PCR mixture included nucleoside triphosphates (including dUTP), DNA polymerase, 0.1 µM each of selective primer, 0.1-0.7 µM common primer, a detection probe, target DNA (9900 copies of wild-type K562 cell line with 100 copies of mutant plasmid, or 10,000 copies of wild-type cell line DNA or 10,000 copies of NRAS wild-type exon 2 or 3 plasmid), and uracil-N-glycosylase. Amplification and analysis were done using the Roche LightCycler® 480 instrument (Roche Applied Science, Indianapolis, Ind.) The following temperature profile was used: 2 cycles of 95° C. (10 seconds) to 62° C. (30 seconds) followed by cycling from 93° C. (10 seconds) to 62° C. (30 seconds) 55 times. Fluorescence data was collected at the start of each 62° C. step in the 55-cycle program.

Results are shown in FIG. 1. Amplification of the wild-type genomic DNA is shown by dashed lines; amplification of the plasmid containing the wild-type sequence is shown by bold solid lines and amplification of the mutant DNA (target

TABLE 2

Primers and probes for exon 2 of the NRAS gene used in Example 1.

| SEQ ID NO: | Function | Sequence 5'-3' |
|---|---|---|
| SEQ ID NO: 6 | 35G > C AS primer | CTGGTGGTGGTTGGAGCCGC |
| SEQ ID NO: 7 | 35G > C AS primer | CTGCTGGTGGTTGGAGEAGC |
| SEQ ID NO: 8 | 35G > C AS primer | CTGCTGGTGGTTGGAGCMGC |
| SEQ ID NO: 9 | 34G > T AS primer | CAAACTGGTGGTGGTTGGAGCTT |
| SEQ ID NO: 10 | 34G > T AS primer | TACAAACTGGTGGTGGTTGGAGCTT |
| SEQ ID NO: 11 | 34G > T AS primer | CAGAGTGGTGGTGGTTGGAGCDT |
| SEQ ID NO: 12 | 35G > A AS primer | AAGTGGTGGTGGTTGGAGCDGA |
| SEQ ID NO: 13 | 35G > A AS primer | AACTTGGTGGTGGTTGGAGTMGA |
| SEQ ID NO: 14 | 35G > A AS primer | AACTGGTGGTGGTTGGAGCTGA |
| SEQ ID NO: 15 | 34G > C AS primer | AACTGGTGGTGGTTGGAACAC |
| SEQ ID NO: 16 | 34G > C AS primer | AACTGGTGGTGGTTGGATCAC |
| SEQ ID NO: 17 | 34G > C AS primer | ATCGGGTGGTGGTTGGAGFAC |
| SEQ ID NO: 18 | 34G > A AS primer | CAGACTGGTGGTGGTTGGAGFAA |
| SEQ ID NO: 19 | 34G > A AS primer | AGACTGGTGGTGGTTGGAGCDA |
| SEQ ID NO: 20 | 34G > A AS primer | AGACTGGTGGTGGTTGGAGFAA |
| SEQ ID NO: 21 | 35G > T AS primer | AACTGGTGGTGGTTGGAGCAAT |
| SEQ ID NO: 22 | 35G > T AS primer | AACTGGTGGTGGTTGGAGCATT |
| SEQ ID NO: 23 | 35G > T AS primer | AACTGGTGGTGGTTGGAGEAAT |
| SEQ ID NO: 24 | Exon 2 common | GAATATGGGTAAAGATGATCCGACAA |
| SEQ ID NO: 25 | Exon 2 common | GTAAAGATGATCCGACAAGTGAGAGA |
| SEQ ID NO: 26 | Exon 2 common | GAATATGGGTAAAGATGATCCGACAAGT |
| SEQ ID NO: 27 | Exon 2 probe | JCACTGAECAATCCAGCTAATCCAGAACCACP |
| SEQ ID NO: 28 | Exon 2 probe | JCACTGAECAATCCAGCTAATCCAGAACCACP |
| SEQ ID NO: 29 | Exon 2 probe | JGTGGTTECTGGATTAGCTGGATTGTCAGTGP |

Key:
AS primer: allele-specific primer,
Common: common primer, E = N4-Methyl-dC, M = N6-Methyl-dA, D = N6-tertiary-butyl-benzyl-dA, F = N4-tertiary-butyl-benzyl-dC, J = HEX, Q = BHQ-2, P = Phosphate sequence) is shown by narrow solid lines. The results demonstrate that when an upstream mutation-specific primer was paired with one of the downstream primers selected from among SEQ ID NOs: 24-26, breakthrough amplification of the non-target (wild-type) sequence was detected. See FIG. 1A (dashed line). When the same mutation-specific primer was paired with a different downstream primer, selected from among SEQ ID NOs: 1-5, breakthrough amplification of the non-target (wild-type) sequence was suppressed, see FIG. 1B. Notably, amplification of the non-target sequence present in a plasmid is unaffected and is not suppressed (bold solid line).

Example 2

Suppression of Breakthrough Amplification by an Additional Suppressor Oligonucleotide In this example, suppression of breakthrough amplification was observed in an AS-PCR targeting mutations in codon 61 of the human NRAS gene. The primers and probes used in Example 2 are shown in Table 3. An upstream primer selected from among SEQ ID NOs: 30-47 is matched to one of the mutations 183A>T, 183A>C, 181C>A, 182A>T, 182A>C, 182A>G corresponding to amino acid changes Q61Ha, Q61Hb, Q61K, Q61L, Q61P, and Q61R in the human NRAS gene and is mismatched with the wild-type sequence. A downstream primer selected from among SEQ ID NOs: 48-50 and detection probe selected from among SEQ ID NOs: 51-53 are common between the mutant and wild-type sequences in exon 3 of the NRAS gene. Suppressor oligonucleotides selected from among SEQ ID NOs: 1-5 do not hybridize to any of the amplicons defined by the primer pairs used in this example.

TABLE 3

Primers and probes for exon 3 of the NRAS gene used in Example 2.

| SEQ ID NO: | Function | Sequence 5'-3' |
|---|---|---|
| SEQ ID NO: 30 | 183A > T AS primer | GGATATACTGGATACAGCTGGACDT |
| SEQ ID NO: 31 | 183A > T AS primer | GGACATACTGGATACAGCTGGACTT |
| SEQ ID NO: 32 | 183A > T AS primer | GGACATACTGGATACAGCTGGAGAT |
| SEQ ID NO: 33 | 183A > C AS primer | ACATACTGGATACAGCTGGACTC |
| SEQ ID NO: 34 | 183A > C AS primer | ATACTGGATACAGCTGGACTC |
| SEQ ID NO: 35 | 183A > C AS primer | ATACTGGATACAGCTGGATAC |
| SEQ ID NO: 36 | 181C > A AS primer | TGGATATACTGGATACAGCTGIAA |
| SEQ ID NO: 37 | 181C > A AS primer | GACATACTGGATACAGCTGGAA |
| SEQ ID NO: 38 | 181C > A AS primer | TGGATATACTGGATACAGCTGGMA |
| SEQ ID NO: 39 | 182A > T AS primer | GAGATACTGGATACAGCTGGAFT |
| SEQ ID NO: 40 | 182A > T AS primer | GACATACTGGATACAGCTGTACT |
| SEQ ID NO: 41 | 182A > T AS primer | GACATACTGGATACAGCTGAACT |
| SEQ ID NO: 42 | 182A > C AS primer | GACGTACTGGATACAGCTGGAFC |
| SEQ ID NO: 43 | 182A > C AS primer | CGTACTGGATACAGCTGGAFC |
| SEQ ID NO: 44 | 182A > C AS primer | GACATACTGGATACAGCTGAACC |
| SEQ ID NO: 45 | 182A > G AS primer | GACATACTGGATACAGCTGGTEG |
| SEQ ID NO: 46 | 182A > G AS primer | ACGTACTGGATACAGCTGGAFG |
| SEQ ID NO: 47 | 182A > G AS primer | GACACACTGGATACAGCTGGAFG |
| SEQ ID NO: 48 | Exon 3 common | AGAGAAAATAATGCTCCTAGTACCTGTAG |
| SEQ ID NO: 49 | Exon 3 common | TCCTTTCAGAGAAAATAATGCTCCTAGT |
| SEQ ID NO: 50 | Exon 3 common | GTTAATATCCGCAAATGACTTGCTATTATT |
| SEQ ID NO: 51 | Exon 3 probe | JCTGTCCETCATGTATTGGTCTCTCATGGCACTGP |
| SEQ ID NO: 52 | Exon 3 probe | JCTCATGETATTGGTCTCTCATGGCACTGTACP |
| SEQ ID NO: 53 | Exon 3 probe | JCTTCGCECTGTCCTCATGTATTGGTCTCTCP |

Key:
AS primer: allele-specific primer,
Common: common primer, E = N4-Methyl-dC, M = N6-Methyl-dA, D = N6-tertiary-butyl-benzyl-dA, F = N4-tertiary-butyl-benzyl-dC, I = Inosine, J = FAM, Q = BHQ-2, P = Phosphate In this example, the same reaction conditions were used as in Example 1, except in addition to the upstream and downstream primer, one of the suppressor oligonucleotides selected from among SEQ ID NOs: 1-5 was added to the reaction at 0.1 or 0.7 µM.

Figure 2A:
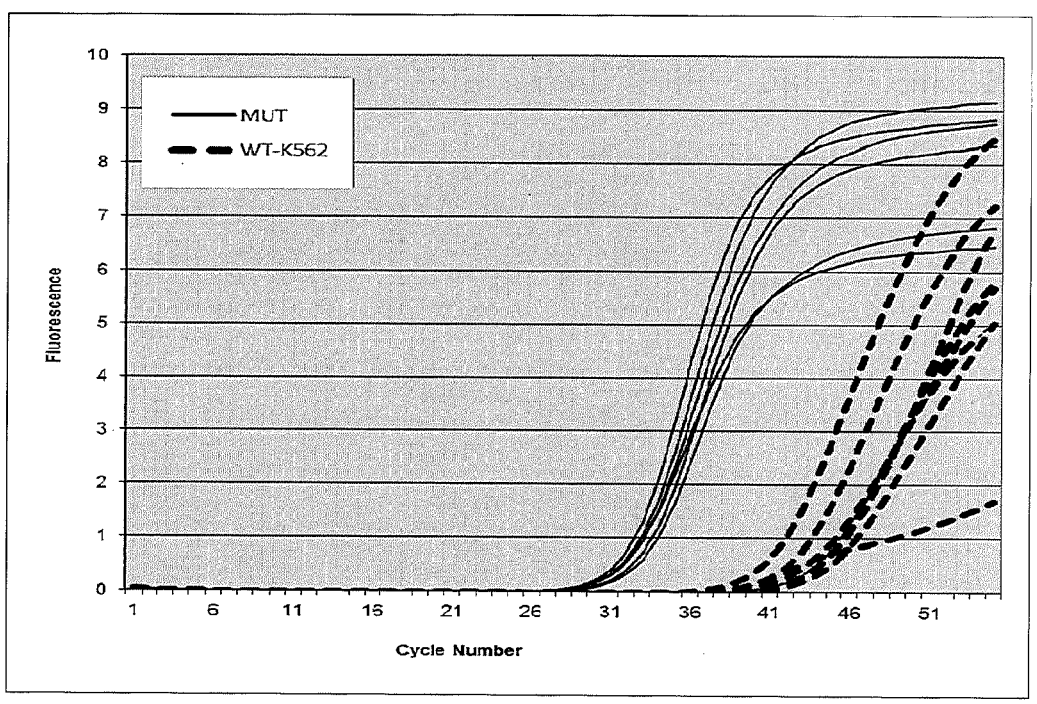
FIG. 2A shows no suppression of the breakthrough amplification without the suppressor oligonucleotide.
Figure 2B:
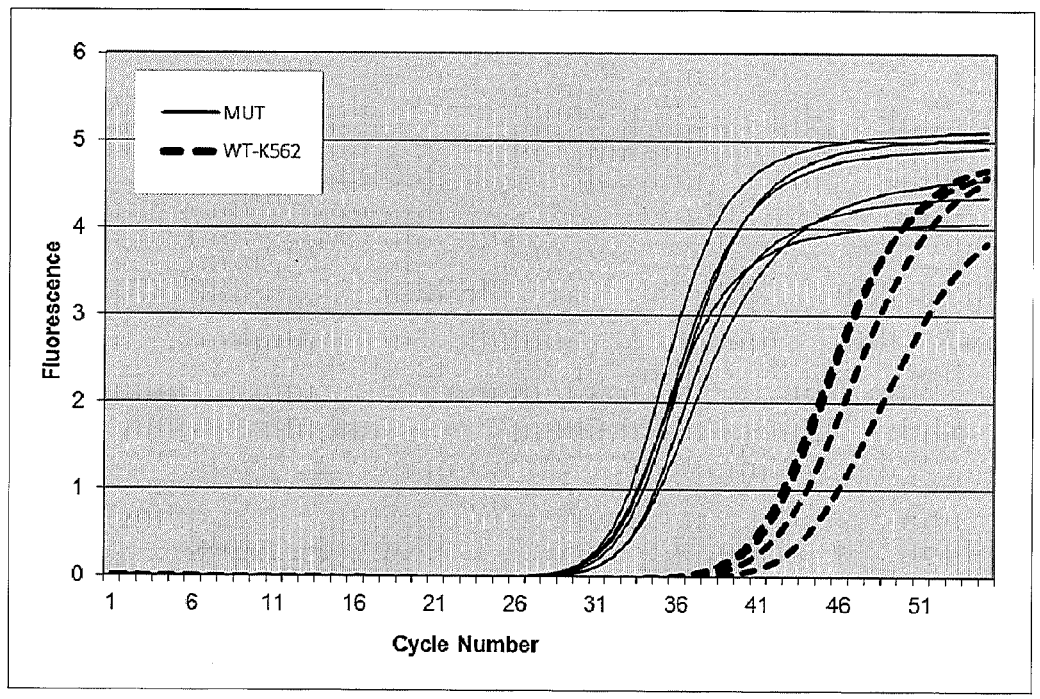
FIG. 2B shows no suppression when the suppressor oligonucleotide was present at low concentration and FIG. 2C shows suppression when the suppressor oligonucleotide was present at a higher relative concentration.
Figure 2C:
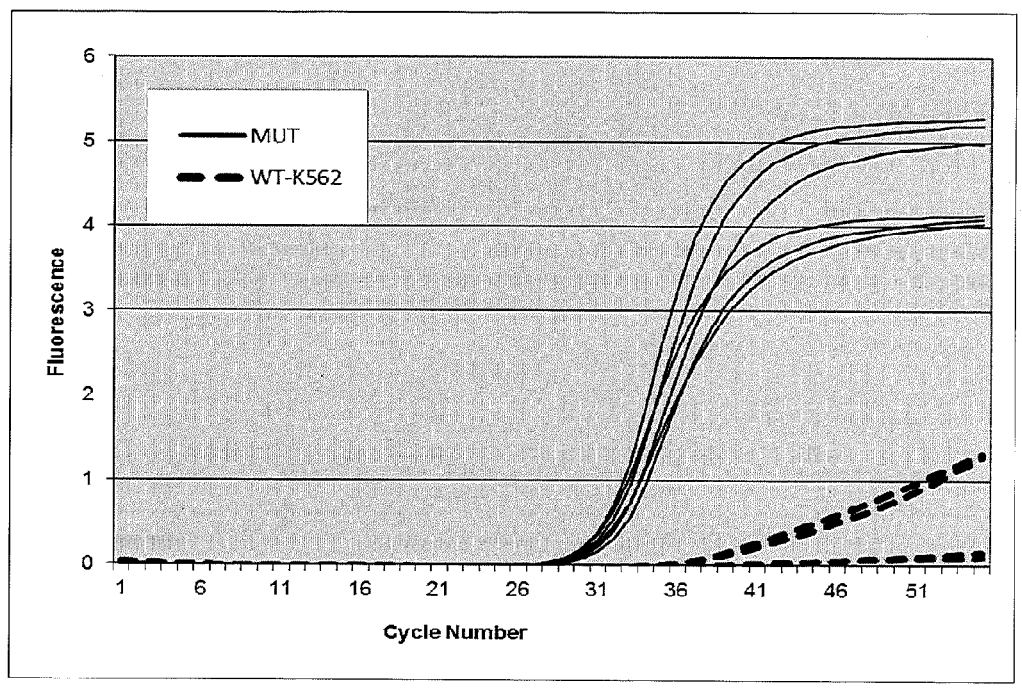

Results are shown in FIG. 2. Amplification of the wild-type genomic DNA is shown by dashed lines and amplification of the mutant DNA (target sequence) is shown by narrow solid lines. The results demonstrate that when the primer pair composed of a common primer and a Q61 mutation-specific primer was used, breakthrough amplification of the non-target sequences was detected. See FIG. 2A (dashed lines). When the suppressor oligonucleotide was also present in the reaction mixture at 0.1 µM, breakthrough amplification of the non-target sequences was not suppressed, see FIG. 2B. But when the suppressor oligonucleotide was present in the reaction mixture at 0.7 µM, breakthrough amplification of the non-target sequences was suppressed, see FIG. 2C. In this example, all the primers are present at 0.1 µM while the suppressing oligonucleotide was present either at 0.1 µM or 0.7 µM.

Example 3

Suppression of Breakthrough Amplification of the Unrelated Template PI3KCA by a Suppressor Oligonucleotide In this example, suppression of breakthrough amplification was observed in an AS-PCR targeting mutations in codon 1049 of the human PI3KCA gene. The primers and probes used in Example 3 are shown in Table 4. An upstream primer selected from among SEQ ID NOs: 54-56 is matched to the mutation 3145G>C corresponding to the amino acid change G1049R in the human PI3KCA gene and is mismatched with the wild-type sequence. A downstream primer selected from among SEQ ID NOs: 57-59 and a probe selected from among SEQ ID NOs: 60 & 96 and 61 & 97 are common between the mutant and wild-type sequences. Suppressor oligonucleotides selected from among SEQ ID NOs: 1-5 (specific for the human NRAS gene) do not hybridize to the PI3KCA amplicons used in this example.

In this example, the same reaction conditions were used as in Example 1, except in addition to the upstream and downstream primer, one of the suppressor oligonucleotides selected from among SEQ ID NOs: 1-5 was added to the reaction at 1.0 µM.

Figure 3A:
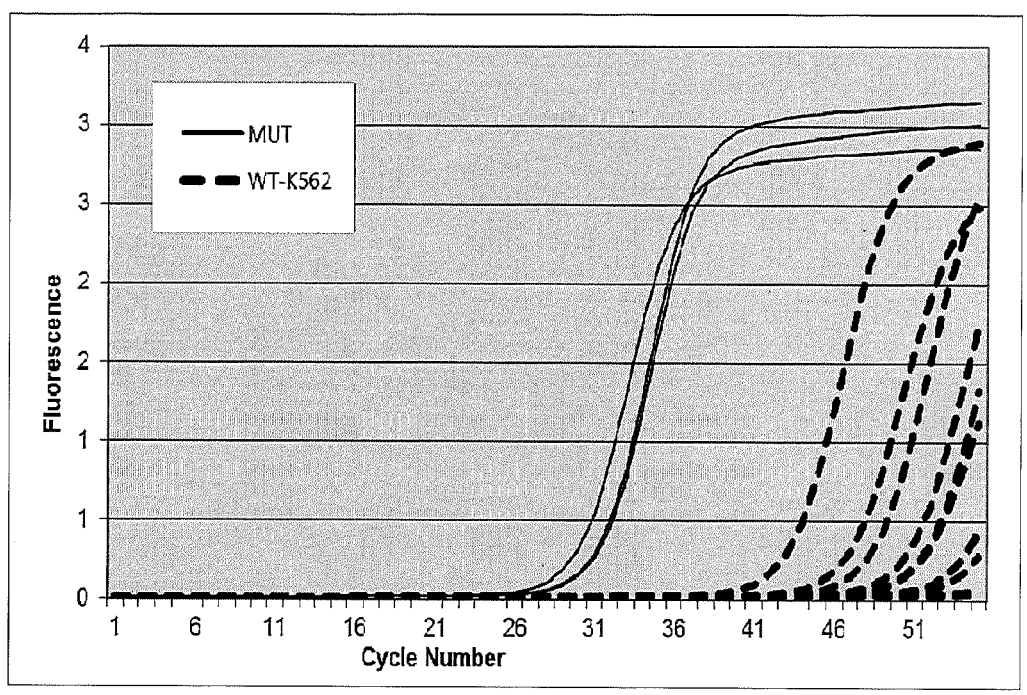
FIG. 3A shows breakthrough amplification in the absence of the suppressor oligonucleotide and FIG. 3B shows suppression of the breakthrough amplification in the presence of the suppressor oligonucleotide.
Figure 3B:
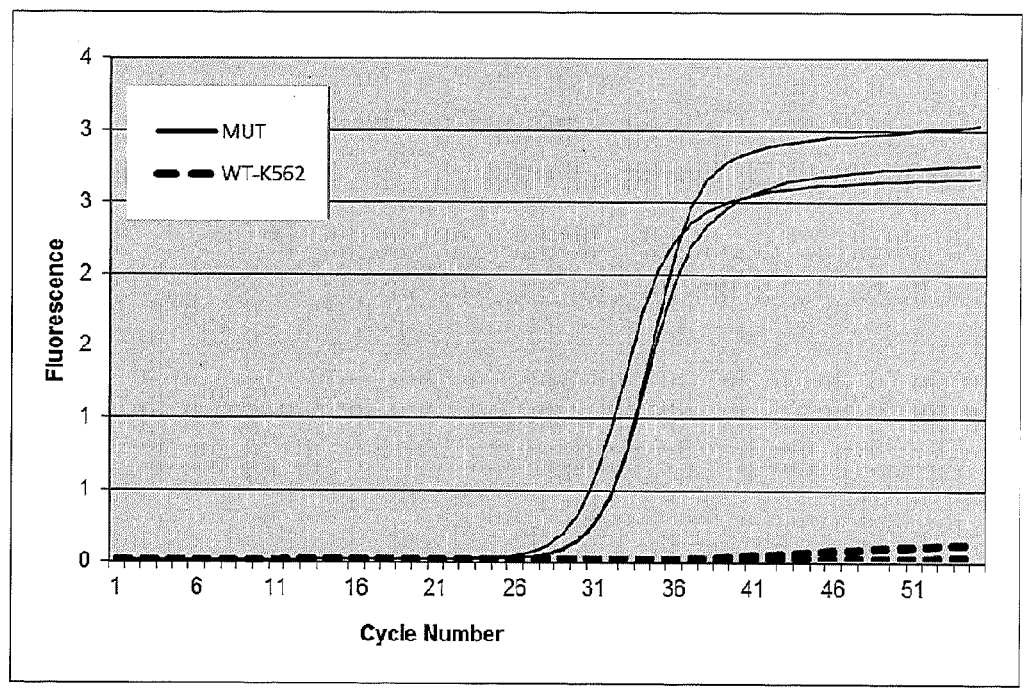
Figure 4A:
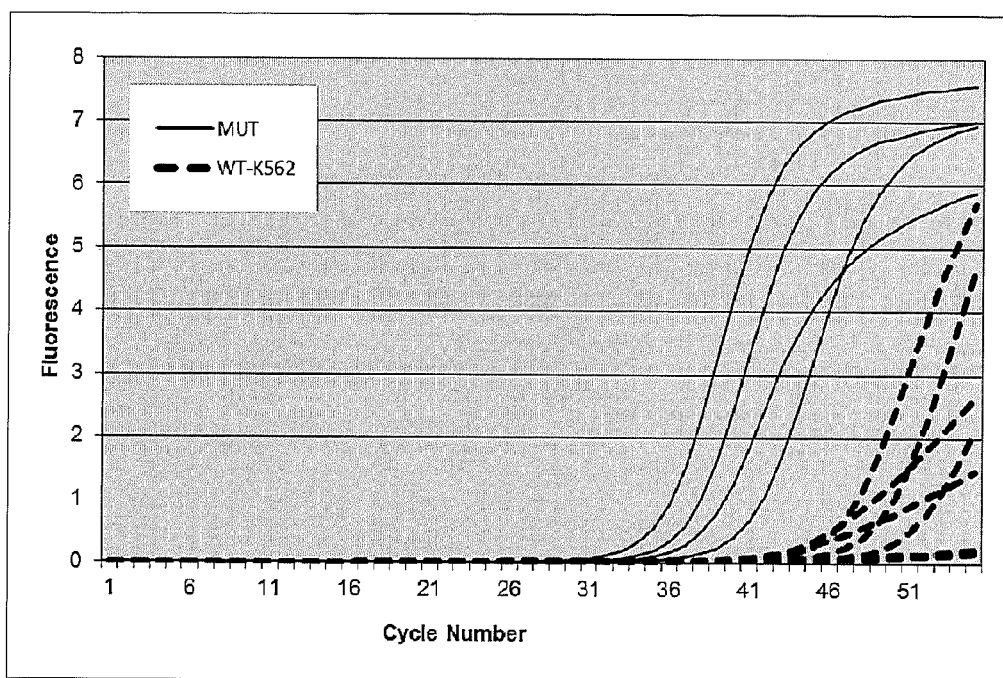
FIG. 4A shows breakthrough amplification in the absence of the suppressor oligonucleotide and FIG. 4B shows suppression of the breakthrough amplification in the presence of the suppressor oligonucleotide in the codon 469 reaction.
Figure 4B:
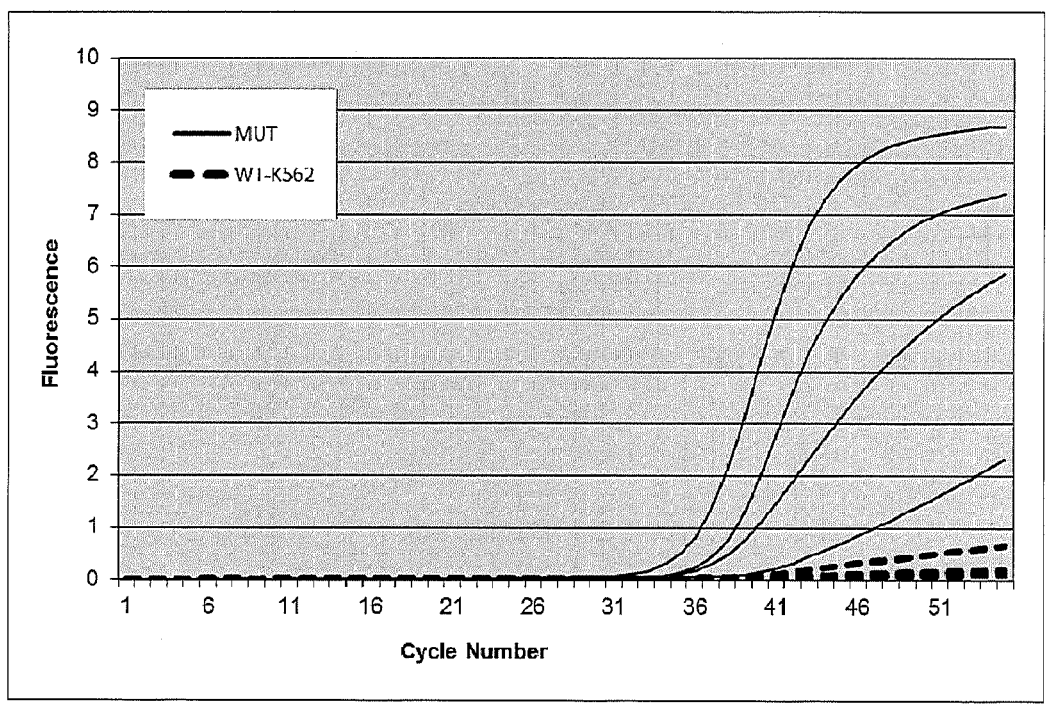
Figure 4C:
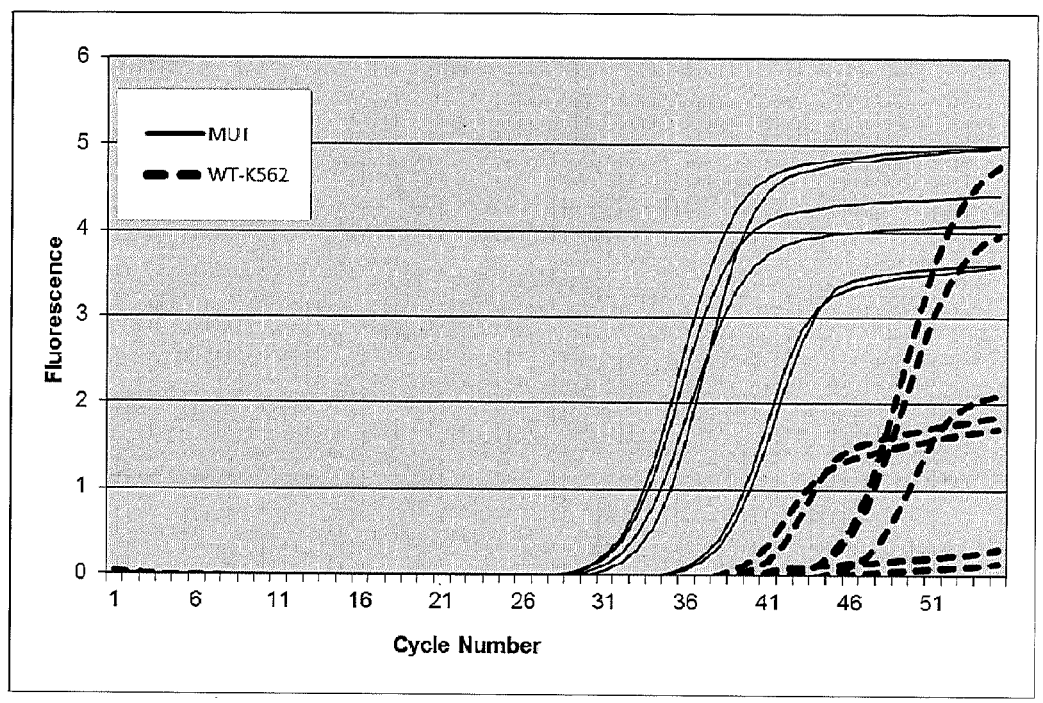
FIG. 4C shows breakthrough amplification in the absence of the suppressor oligonucleotide and FIG. 4D shows suppression of the breakthrough amplification in the presence of the suppressor oligonucleotide in the codon 600 reaction.
Figure 4D:
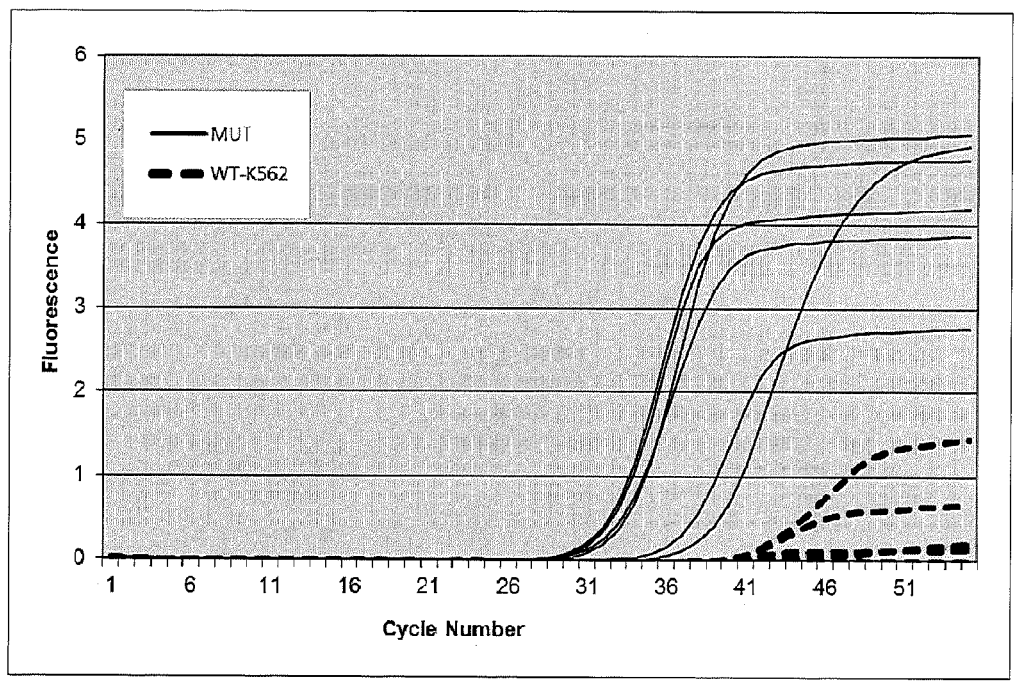

Results are shown in FIG. 3. Amplification of the wild-type genomic DNA is shown by dashed lines; and amplification of the mutant DNA (target sequence) is shown by narrow solid lines. The results demonstrate that when the primer pair composed of a G1049R-specific primer and a common primer was used, breakthrough amplification of the non-target (wild-type) sequence was detected. See FIG. 3A (dashed lines). When the suppressor oligonucleotide selected from among SEQ ID NOs: 1-5 was also present in the reaction mixture, breakthrough amplification of the non-target (wild-type) sequence was suppressed, with no impact on the specific amplification of the target (mutant G1049R) sequence (solid lines). See FIG. 3B. The same suppressing oligonucleotide selected from among SEQ ID NOs: 1-5 was also added to allele-specific PCR designed to detect PI3KCA mutations 1258T>C, 1635G>T, 1634A>G, and 1633G>A. The same trend was observed: no impact on specific amplification of the target (mutant) sequence and suppression of the breakthrough amplification of the non-target (wild-type) sequence (data not shown).

Example 4

Suppression of Breakthrough Amplification of the Unrelated Template BRAF by a Suppressor Oligonucleotide In this example, partial suppression of breakthrough amplification was observed in an AS-PCR targeting mutations in codons 469 and 600 of the human BRAF gene. The primers and probes used in Example 4 are shown in Table 5. For mutations in codon 469, the upstream primer was selected from among SEQ ID NOs: 62-70. These primers are matched to various mutations at codon 469 in exon 11. For mutations in codon 600, the upstream primer was selected from among SEQ ID NOs: 75-86. These primers are matched to various mutations at codon 600 in exon 15. For the codon 469 mutations, the common downstream primer was selected from

TABLE 4

Primers and probes for the PI3KCA gene used in Example 3.

| SEQ ID NO: | Function | Sequence 5'-3' |
|---|---|---|
| SEQ ID NO: 54 | 3145G > C AS primer | CATGAAACAAATGAATGATGCACATCCTC |
| SEQ ID NO: 55 | 3145G > C AS primer | CATGAAACAAATGAATGATGCACATCGTC |
| SEQ ID NO: 56 | 3145G > C AS primer | CATGAAACAAATGAATGATGCACATTATC |
| SEQ ID NO: 57 | 3145 common | CAATGCATGCTGTTTAATTGTGTGGA |
| SEQ ID NO: 58 | 3145 common | TTCAGTTCAATGCATGCTGTTTAATTGTG |
| SEQ ID NO: 59 | 3145 common | GTGGAATCCAGAGTGAGCTTTCAT |
| SEQ ID NOS 60 and 96 | 3145 probe | JTGGCTGGACAAQCAAAAATGGATTGGATCP |
| SEQ ID NOS 61 and 97 | 3145 probe | JATGGATTGGAQTCTTCCACACAATTAAACAGCATGP |

KEY
AS primer: allele-specific primer,
Common: common primer, J = JA270, Q = BHQ-2, P = Phosphate among SEQ ID NOs: 71-72, and the probe was selected from among SEQ ID NOs: 73 & 98 and 74 & 99. For the codon 600 mutations, the downstream primer was selected from among SEQ ID NOs: 87-89, and the probe was selected from among SEQ ID NOs: 90-92. Suppressor oligonucleotides selected from among SEQ ID NOs: 1-5 (specific for the human NRAS gene) do not hybridize to the BRAF amplicons defined by any of the primer pairs used in this example.

TABLE 5

Primers and probes for the BRAF gene used in the Example 4.

| SEQ ID NO: | Function | Sequence 5'-3' |
|---|---|---|
| SEQ ID NO: 62 | 1406G > C AS primer | AAAGAATTGGATCTGGATCATTAGC |
| SEQ ID NO: 63 | 1406G > C AS primer | AAAGAATTGGATCTGGATCATTCGC |
| SEQ ID NO: 64 | 1406G > C AS primer | AAAGAATTGGATCTGGATCATGTGC |
| SEQ ID NO: 65 | 1405G > A AS primer | AAAGAATTGGATCTGGATCATATA |
| SEQ ID NO: 66 | 1405G > A AS primer | ACAAAGAATTGGATCTGGATCATTAA |
| SEQ ID NO: 67 | 1406G > T AS primer | AGTGGGACAAAGAATTGGATCAGT |
| SEQ ID NO: 68 | 1406G > T AS primer | AGTGGGACAAAGAATTGGATCTAT |
| SEQ ID NO: 69 | 1406G > A AS primer | ACAAAGAATTGGATCTGGATCATTTAA |
| SEQ ID NO: 70 | 1406G > A AS primer | GACAAAGAATTGGATCTGGATCATTTAA |
| SEQ ID NO: 71 | Exon 11 Common | GCGAACAGTGAATATTTCCTTTGATG |
| SEQ ID NO: 72 | Exon 11 Common | GACTTGTCACAATGTCACCACATTACATA |
| SEQ ID NOS 73 and 98 | Exon 11 Probe | EAGTCTACAAGQGGAAAGTGGCATGGTAAP |
| SEQ ID NOS 74 and 99 | Exon 11 Probe | ETGGCATGGTAQAGTATGTAATGTGGTGACATTP |
| SEQ ID NO: 75 | 1798_1799GT > AA, 1798_1799GT > AG, 1798G > A AS primer | AGTAAGAATAGGTGATTTTGGTCTAGCTACFA |
| SEQ ID NO: 76 | 1798_1799GT > AA, 1798_1799GT > AG, 1798G > A AS primer | AGTAAGAATAGGTGATTTTGGTCTAGCTALAA |
| SEQ ID NO: 77 | 1798_1799GT > AA, 1798_1799GT > AG, 1798G > A AS primer | AGTAAGAATAGGTGATTTTGGTCTAGCTCLAA |
| SEQ ID NO: 78 | 1798G > T AS primer | AGTAAGAATAGGTGATTTTGITCTAGCTACFT |
| SEQ ID NO: 79 | 1798G > T AS primer | AGTAAGAATAGGTGATTTTGGTCTAICTACFT |
| SEQ ID NO: 80 | 1798G > T AS primer | AGTAAGAATAGGTGATTTTGGTCTAGCTACFT |
| SEQ ID NO: 81 | 1799T > G AS primer | AATGGGTGATTTTGGTCTAGCTFCTGG |
| SEQ ID NO: 82 | 1799T > G AS primer | AATGGGTGATTTTGGTCTAGCTFTAIG |
| SEQ ID NO: 83 | 1799T > G AS primer | AGTAGGTGATTTTGGTCTAGCTATFGG |
| SEQ ID NO: 84 | 1799T > C AS primer | AATGGGTGATTTTGGTCTAGCTFTAIC |
| SEQ ID NO: 85 | 1799T > C AS primer | AATGGGTGATTTTGGTCTAGCTALTIC |
| SEQ ID NO: 86 | 1799T > C AS primer | AATGGGTGATTTTGGTCTAGCTALTGC |
| SEQ ID NO: 87 | Exon 15 Common | GTGGAAAATAGCCTCAATTCTTACCA |
| SEQ ID NO: 88 | Exon 15 Common | TAGCCTCAATTCTTACCATCCACAAAA |
| SEQ ID NO: 89 | Exon 15 Common | CTAGTAACTCAGCAGCATCTCAG |
| SEQ ID NO: 90 | Exon 15 Probe | ETGGATCQCAGACAACTGTTCAAACTGATGGGP |

TABLE 5-continued

Primers and probes for the BRAF gene used in the Example 4.

| SEQ ID NO: | Function | Sequence 5'-3' |
|---|---|---|
| SEQ ID NO: 91 | Exon 15 Probe | ETCCCATQCAGTTTGAACAGTTGTCTGGATCCAP |
| SEQ ID NO: 92 | Exon 15 Probe | ETCTCGATGGAGTGGGTCCQP |

KEY
AS primer: allele-specific primer,
Common: common primer, F = N6-tertiary-butyl-benzyl-dA, L = N4-tertiary-butyl-benzyl-dC, I = Inosine, E = FAM, Q = BHQ-2, P = Phosphate In this example, the same reaction conditions were used as in Example 3.

Results are shown in FIG. 4. Amplification of the wild-type genomic DNA is shown by dashed lines and amplification of the BRAF codon 469 and 600 targets is shown by solid lines. The results demonstrate that when the primer pair consisting of a primer matched to one of the codon 469 mutations and a common primer was used, breakthrough amplification of the non-target (wild-type) sequence was detected, see FIG. 4A (dashed lines). When a suppressor oligonucleotide selected from among SEQ ID NOS: 1-5 was also present in the reaction mixture, breakthrough amplification of the non-target (wild-type) sequence was suppressed (dashed lines,) with slight impact on the specific amplification of the mutant sequence (solid lines). See FIG. 4B. When the primer pair consisting of a primer matched to one of the codon 600 mutations and a common primer was used, breakthrough amplification of the non-target (wild-type) sequence was detected. See FIG. 4C (dashed lines). When a suppressor oligonucleotide selected from among SEQ ID NOs: 1-5 was also present in the reaction mixture, breakthrough amplification of the non-target (wild-type) sequence was partially suppressed see FIG. 4D. Incomplete suppression of the non-target amplification and slight impact on the target amplification observed with the BRAF system suggests that the suppression phenomenon may be sequence-dependent.

Example 5

Suppression of Breakthrough Amplification by Linear Primer Extension Reactions

In this example, suppression of breakthrough amplification of the NRAS template was observed in the presence of the M13 template and a series of M13-specific primers. The AS-PCR targeted mutations in codons 12 and 61 of the human NRAS gene. The M13 primers used in Example 5 are shown in Table 6. For the NRAS target, the upstream primer was selected from among SEQ ID NOs: 30-47. These primers are matched to one of the mutations 183A>T, 183A>C, 181C>A, 182A>T, 182A>C, 182A>G corresponding to amino acid changes Q61Ha, Q61Hb, Q61K, Q61L, Q61P, and Q61R in the human NRAS gene and are mismatched with the wild-type sequence. The downstream primer selected from among SEQ ID NOs: 48-50 and the probe selected from among SEQ ID NOs: 51-53 are common between the mutant and wild-type sequences of exon 3 in the human NRAS gene. The upstream primer selected from among SEQ ID NOs: 6-23, is matched to one of the mutations 35G>C, 34G>T, 35G>A, 34G>C, 34G>A, and 35G>T in exon 2 of the human NRAS gene and is mismatched with the wild-type sequence. The downstream primer selected from SEQ ID NOs: 24-26 and the detection probe selected from SEQ ID NOs: 27-29 are common between the mutant and wild-type sequences of exon 2 in the human NRAS gene. The reaction mixture also contained single-stranded circular DNA of bacteriophage M13 and three primers (SEQ ID NOs: 93-95, Table 6) oriented in the same direction to ensure linear amplification of the viral template.

TABLE 6

M13 primers used Example 5.

| SEQ ID NO: | Function | Sequence 5'-3' |
|---|---|---|
| SEQ ID NO: 93 | M13 Primer | ACATGAAAGTATTAAGAGGCTGAGACTCCTCA |
| SEQ ID NO: 94 | M13 Primer | GAAGAAAGCGAAAGGAGCGGGC |
| SEQ ID NO: 95 | M13 Primer | GGAACGAGGGTAGCAACGGCTACA |

In this example, the same reaction conditions were used as in Example 1, except the M13 single stranded bacteriophage template was added at 10,000 copies per reaction, and primers, SEQ ID NOs: 63-65, were added at equimolar concentrations of 0.033 µM each for a total concentration of 0.1 µM.

Results are shown in FIG. 5. Amplification of the wild-type genomic DNA is shown by dashed lines and amplification of the NRAS codon 12 or codon 61 mutant targets is shown by solid lines. The results demonstrate that when the primer pair consisting of an allele-specific primer matched to one of the mutations in codon 61 and a common primer was used, breakthrough amplification of the non-target (wild-type) NRAS sequence was detected. See FIG. 5A (dashed lines). When the M13 DNA and the three primers capable of linear amplification of the M13 DNA were also present in the reaction mixture, breakthrough amplification of the non-target (wild-type) NRAS sequence was suppressed. See FIG. 5B. By comparison, when the primer pair consisting of an allele-specific primer matched to one of the mutations in codon 12 and a common primer was used, breakthrough amplification of the non-target (wild-type) NRAS sequence was detected. See FIG. 5C (dashed lines). This breakthrough amplification was not suppressed by the M13 DNA and the three primers capable of linear amplification. See FIG. 5D.

Example 6

Breakthrough Suppression by Suppressor Oligonucleotides with Varying Degrees of Homology to the Target Genome In this example, suppression of breakthrough amplification with several suppressor oligonucleotides was observed in an AS-PCR targeting mutations in codon 12 of the human NRAS gene. An upstream primer was selected from among SEQ ID NOs: 6-23, the primers matched to one of the codon 12 mutations (35G>C, 34G>T, 35G>A, 34G>C, 34G>A, and 35G>T, corresponding to amino acid changes G12A, G12C, G12D, G12R, G12S, and G12V) in the human NRAS gene and mismatched with the wild-type sequence. The upstream primer was paired with different downstream primers acting as suppressors of breakthrough amplification. These downstream primers represented by SEQ ID NOs: 1-5 and 24-26, have varying degrees of homology to the target genome ranging between low, medium and high as determined according to the method of the present invention. See Example 8 and FIG. 8.

In this example, the same reaction conditions were used as in Example 1. The suppressor oligonucleotides with low, medium and high homology were used at 0.1 µM.

Figure 6A:
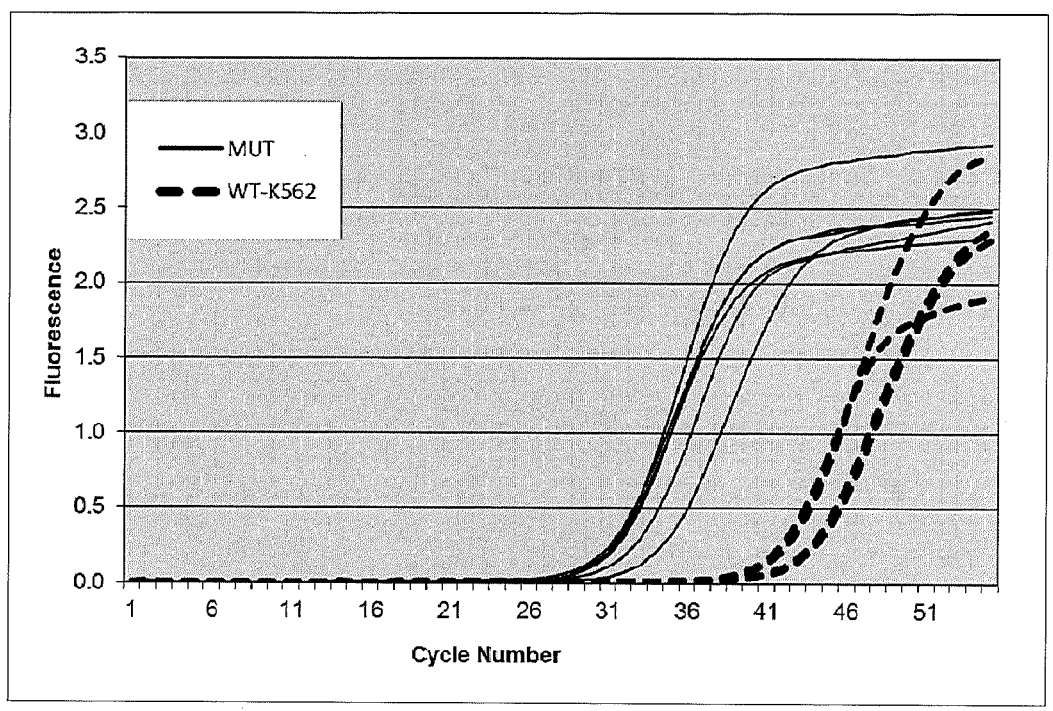
FIG. 6A shows no suppression of the breakthrough amplification by a suppressor oligonucleotide with low degree of homology.
Figure 6B:
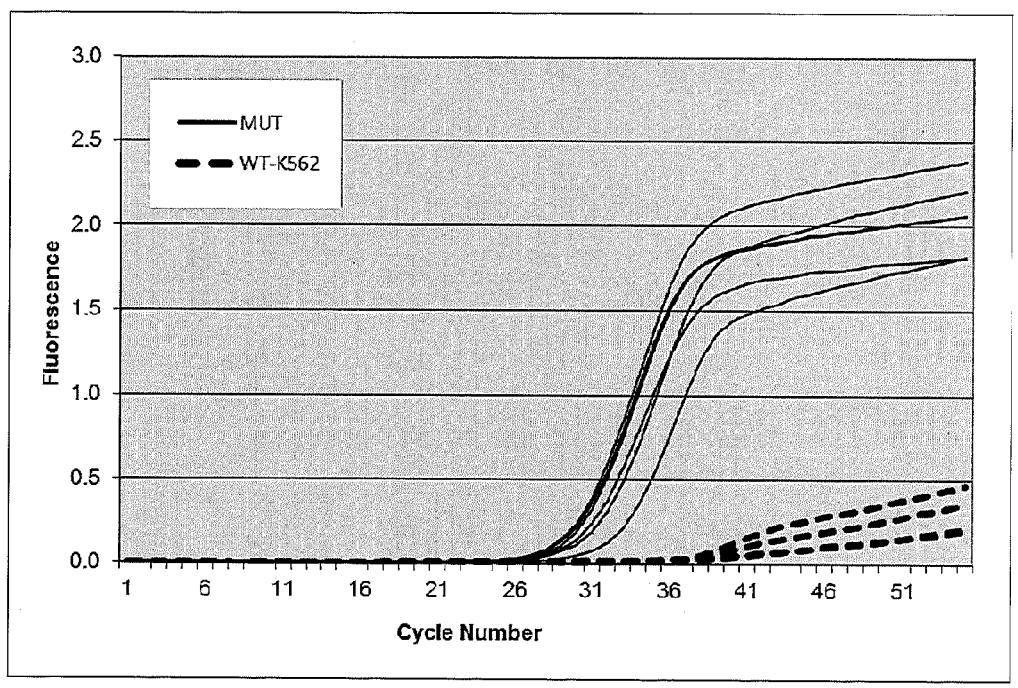
FIG. 6B shows partial suppression by an oligonucleotide with medium degree of homology.
Figure 6C:
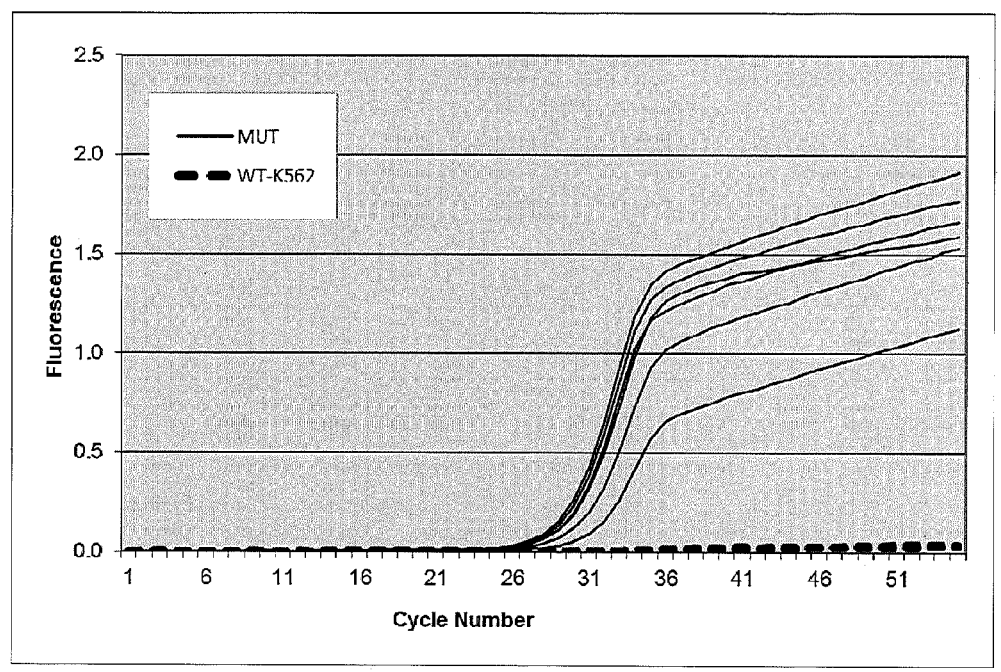
FIG. 6C shows complete suppression by an oligonucleotide with high degree of homology.

Results are shown in FIG. 6. Amplification of the wild-type genomic DNA is shown by dashed lines; amplification of the NRAS codon 12 targets is shown by solid lines. The results demonstrate that the downstream primer with the highest degree of homology to the target genome as determined by the method of the present invention (SEQ ID NO: 1), produced the highest level of suppression (See FIG. 6C), while the downstream primers with the medium degree of homology (SEQ ID NOs: 2-5) produced a lower level of suppression, see FIG. 6B. The downstream primers with the lowest degree of homology (SEQ ID NOs: 24-26) had no effect on wild-type breakthrough and showed no suppression, see FIG. 6A. It is also worth noting that the suppressing oligonucleotides (SEQ ID NOs: 1-5) had varying degrees of suppression, but had no negative impact on the specific amplification as measured by $C_t$.

Example 7

Selecting Regions of Homology within the Region of Interest

In this example, human NRAS gene was selected as the region of interest for designing suppressor oligonucleotides. The 488 base pair region from exon 2 of the NRAS gene was used as a query sequence to be compared to the human genome sequence under relaxed conditions selecting the option that finds "somewhat similar sequences" using the algorithm "blastn." FIG. 7 shows that the search revealed regions of multiple homologies in the portions defined by nucleotides 180-270 and 360-450 of the query sequence. These regions were selected as regions of interest for design of suppressor oligonucleotides.

Example 8

Selecting Suppressor Oligonucleotides from the Region of Interest

In this example, several oligonucleotides from the regions of interest were designed and subjected to a BLAST® analysis to determine regions of homology in the human genome meeting the criteria set forth by the present invention. FIG. 8 shows parameters for each oligonucleotide and the actual ability to suppress breakthrough amplification in reactions. The parameters include the length of the oligonucleotide under the column "nMer". Under the column "Total Hits" is the total number of "Blast Hits" between the oligonucleotide and the target genome with the program Blastn was able to find. The program stringency was set on "somewhat similar sequences". Under the column "Hits with Criteria", this is the total number of hits that meet the criteria of 75% identity and fewer than two mismatches at the 3' terminus. The column "Degree of Homology" contains a value assigned as follows: the degree of homology to the target genome was said to be "low" when there was only one hit that meets the criteria set forth by the present invention, the degree of homology was said to be "medium" when there were ten or fewer hits that meet the criteria, and the degree of homology was said to be "high" when there were more than 10 hits that meet the criteria. Lastly, the "Breakthrough" column indicates whether or not breakthrough amplification was observed in the presence of the oligonucleotide.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A reaction mixture for performing an amplification reaction of a target sequence in the genome of a target organism with reduced amplification of non-target sequences, comprising:
- at least one allele-specific primer specific for a variant of the target sequence;
- an amplicon formed by the at least on allele-specific primer and a reverse primer;
- a suppressor oligonucleotide (a) having no significant similarity with the target sequence as determined by the blastn algorithm for somewhat similar sequences, (b) extendable by a DNA polymerase, and (c) having a sequence comprising at least one region of complementarity to multiple sites in the genome of the target organism, wherein the least one region of complementarity: (i) is at least 15 base pairs long; and (ii) spans the 3'-end of the suppressor oligonucleotide; and
- a fluorescently labeled probe oligonucleotide, wherein the reaction mixture does not include an amplicon formed by the suppressor oligonucleotide.

2. The reaction mixture of claim 1, wherein the suppressor oligonucleotide is selected from a group consisting of SEQ ID NOs: 1-3, and 5.

3. A reaction mixture for performing an amplification reaction of a target sequence in the genome of a target organism with reduced amplification of non-target sequences, comprising:
- at least one allele-specific primer specific for a variant of the target sequence comprising at least one unconventional-base nucleotide;
- an amplicon formed by the at least one allele-specific primer and a reverse primer;
- a suppressor oligonucleotide (a) having no significant similarity with the target sequence as determined by the blastn algorithm for somewhat similar sequences, (b) extendable by a DNA polymerase, and (c) having a sequence comprising at least one region of complementarity to multiple sites in the genome of the target organism, wherein the least one region of complementarity: (i) is at least 15 base pairs long; and (ii) spans the 3'-end of the suppressor oligonucleotide;
- buffer necessary for the function of a DNA polymerase; wherein the reaction mixture does not include an amplicon formed by the suppressor oligonucleotide.

4. The reaction mixture of claim 3, wherein the suppressor oligonucleotide is selected from a group consisting of SEQ ID NOs: 1-3, and 5.

5. The reaction mixture of claim 3, wherein said unconventional-base nucleotide is alkylated.

6. The reaction mixture of claim 1, further comprising nucleotide triphosphates, a DNA polymerase, and a buffer necessary for the function of the polymerase.

7. The reaction mixture of claim 1, further comprising nucleotide triphosphates, a DNA polymerase, and a buffer necessary for the function of the polymerase.

* * * * *